(12) United States Patent
Baba et al.

(10) Patent No.: US 8,372,010 B2
(45) Date of Patent: Feb. 12, 2013

(54) ULTRASONIC DOPPLER DIAGNOSIS DEVICE

(75) Inventors: Tatsuro Baba, Otawara (JP); Yasuo Miyajima, Utsunomiya (JP); Takeshi Sato, Nasushiobara (JP); Tetsuya Kawagishi, Nasushiobara (JP); Yasutsugu Seo, Otawara (JP); Yoshitaka Mine, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 750 days.

(21) Appl. No.: 11/572,696

(22) PCT Filed: Oct. 19, 2005

(86) PCT No.: PCT/JP2005/019227
§ 371 (c)(1),
(2), (4) Date: Jan. 25, 2007

(87) PCT Pub. No.: WO2006/043603
PCT Pub. Date: Apr. 27, 2006

(65) Prior Publication Data
US 2007/0282203 A1    Dec. 6, 2007

(30) Foreign Application Priority Data

Oct. 20, 2004  (JP) ................................ 2004-306009

(51) Int. Cl.
*A61B 8/00* (2006.01)
(52) U.S. Cl. ..................................................... 600/453
(58) Field of Classification Search .......... 600/453–457; 73/584, 587, 589, 596–648
See application file for complete search history.

(56) References Cited

U.S. PATENT DOCUMENTS

| 4,819,652 | A |   | 4/1989 | Micco |         |
|-----------|---|---|--------|-------|---------|
| 5,224,482 | A | * | 7/1993 | Nikoonahad et al. | 600/454 |
| 5,562,097 | A |   | 10/1996 | Yao |         |

(Continued)

FOREIGN PATENT DOCUMENTS

| JP | 3 48789  | 3/1991 |
| JP | 3 162837 | 7/1991 |

(Continued)

OTHER PUBLICATIONS

J. E. Wilhjelm, et al., "Coherent FM Doppler System", Proc. IEEE Ultrason Symp., pp. 903-906, 1989.

(Continued)

*Primary Examiner* — Brian Casler
*Assistant Examiner* — Rajeev Siripurapu
(74) *Attorney, Agent, or Firm* — Oblon, Spivak, McClelland, Maier & Neustadt, L.L.P.

(57) ABSTRACT

There is provided an ultrasonic wave diagnosis instrument. The ultrasonic wave Doppler diagnosis instrument transmits an ultrasonic continuous wave in a range direction and receives a reflective wave of the ultrasonic continuous wave. The ultrasonic wave Doppler diagnosis instrument includes: a modulation unit that subjects the ultrasonic continuous wave to frequency modulation such that a phase is varied in accordance with the distance of the range direction; a demodulation unit that demodulates the reflective wave for each range of the range direction while interlocking with the frequency modulation, and generates a reception signal in the range in a separated state; and a presentation unit that presents information by using a signal of a Doppler component based on the reception signal.

15 Claims, 28 Drawing Sheets

U.S. PATENT DOCUMENTS

| | | | | |
|---|---|---|---|---|
| 5,871,447 A | * | 2/1999 | Ramamurthy et al. | 600/443 |
| 5,920,280 A | * | 7/1999 | Okada et al. | 342/109 |
| 6,121,915 A | * | 9/2000 | Cooper et al. | 342/70 |
| 6,179,781 B1 | * | 1/2001 | Phillips | 600/454 |
| 6,213,947 B1 | * | 4/2001 | Phillips | 600/443 |
| 6,306,093 B1 | * | 10/2001 | Wang | 600/454 |
| 6,606,052 B1 | * | 8/2003 | Miyahara | 342/70 |
| 2004/0264297 A1 | | 12/2004 | Berkman et al. | |

FOREIGN PATENT DOCUMENTS

| | | |
|---|---|---|
| JP | 2000 284047 | 10/2000 |
| JP | 2004-57525 | 2/2004 |

OTHER PUBLICATIONS

U.S. Appl. No. 11/928,498, filed Oct. 30, 2007, Baba, et al.

\* cited by examiner

EXPLANATORY VIEW OF SIX REGION OF TIME
VARIATION OF SPECTRUM

RELATIONSHIP BETWEEN CHIRP FREQUENCY
LOCATION OF Rx MODULATION AND SPECTRUM

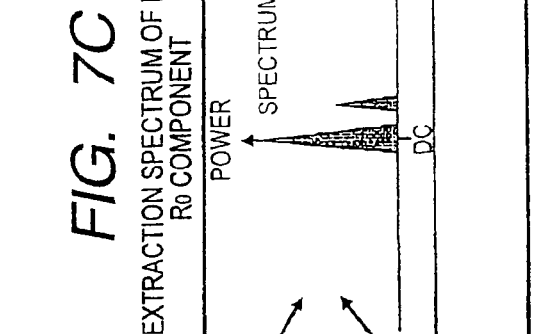
FIG. 7A SPECTRUM OF Rup(t) and Rdn(t)
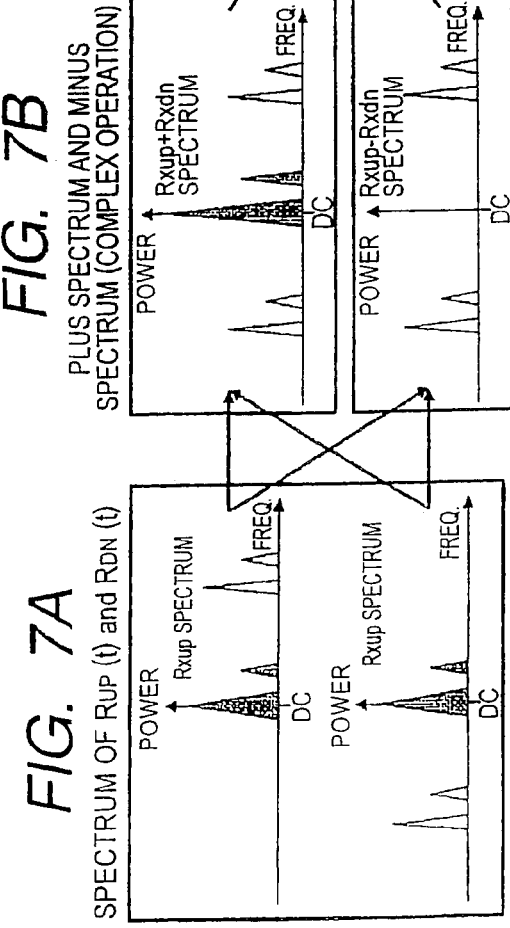
FIG. 7B PLUS SPECTRUM AND MINUS SPECTRUM (COMPLEX OPERATION)
FIG. 7C EXTRACTION SPECTRUM OF RANGE R0 COMPONENT
FIG. 7D SEPARATION BY BAND FILTER
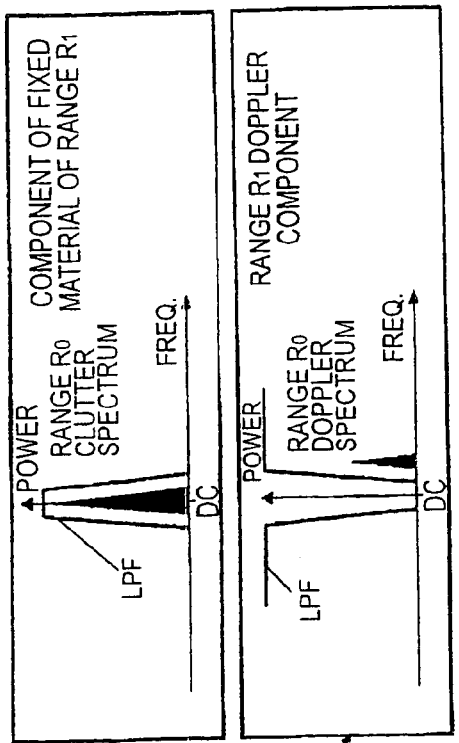
FIG. 7E
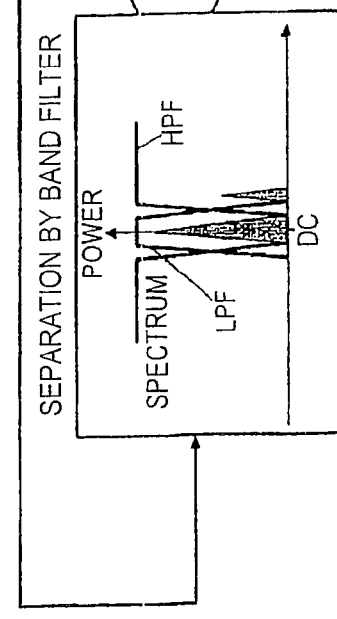

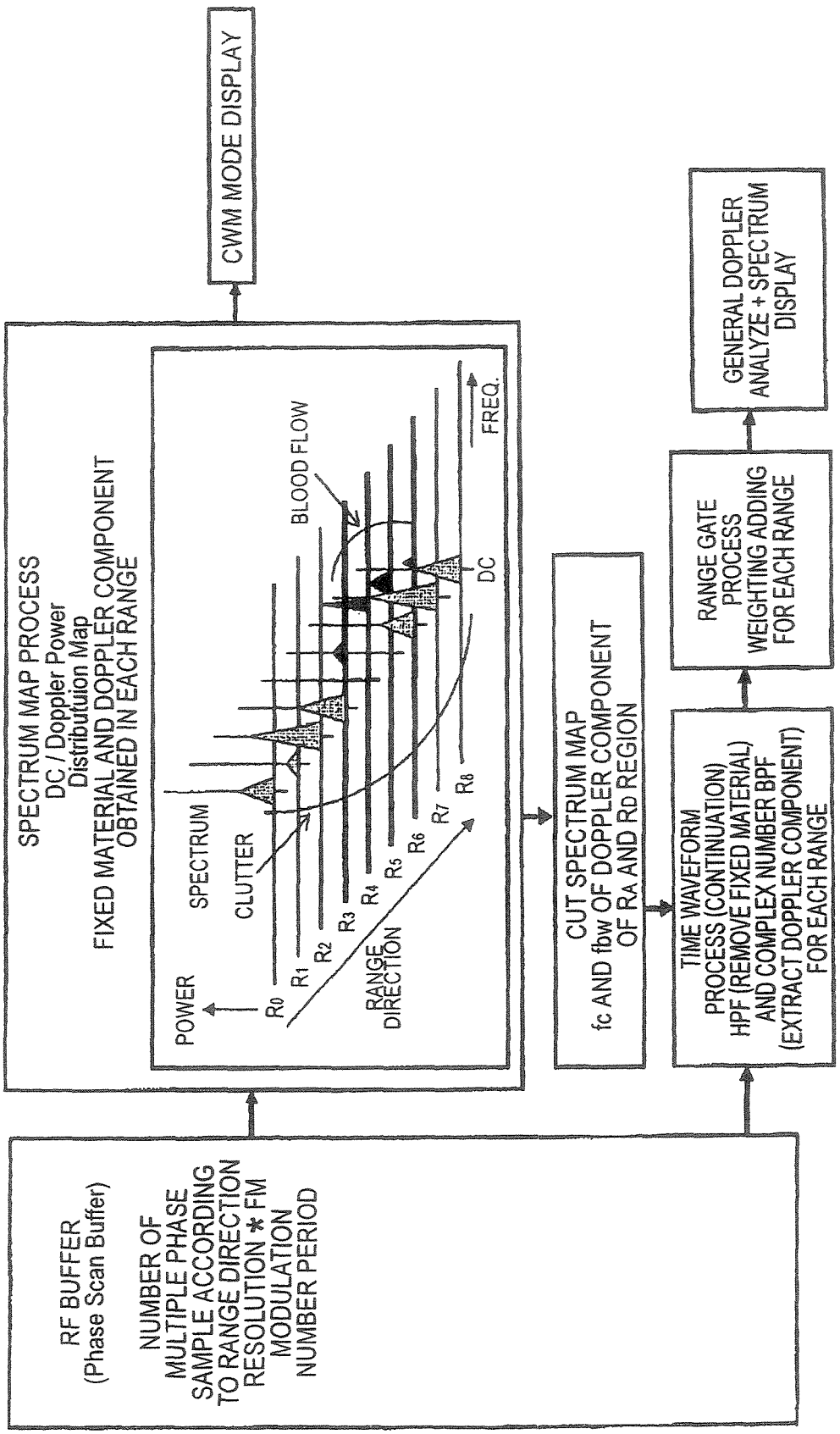

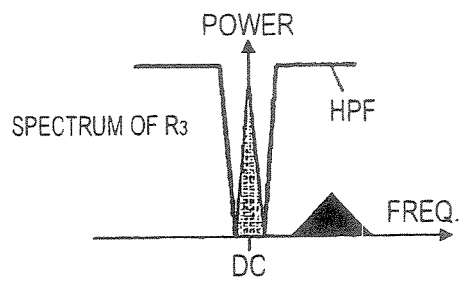
FIG. 15A
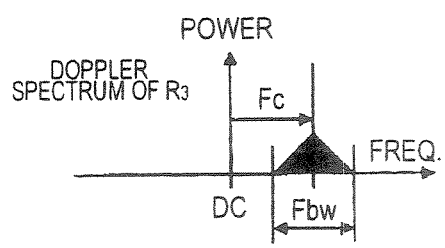
FIG. 15B
FIG. 16
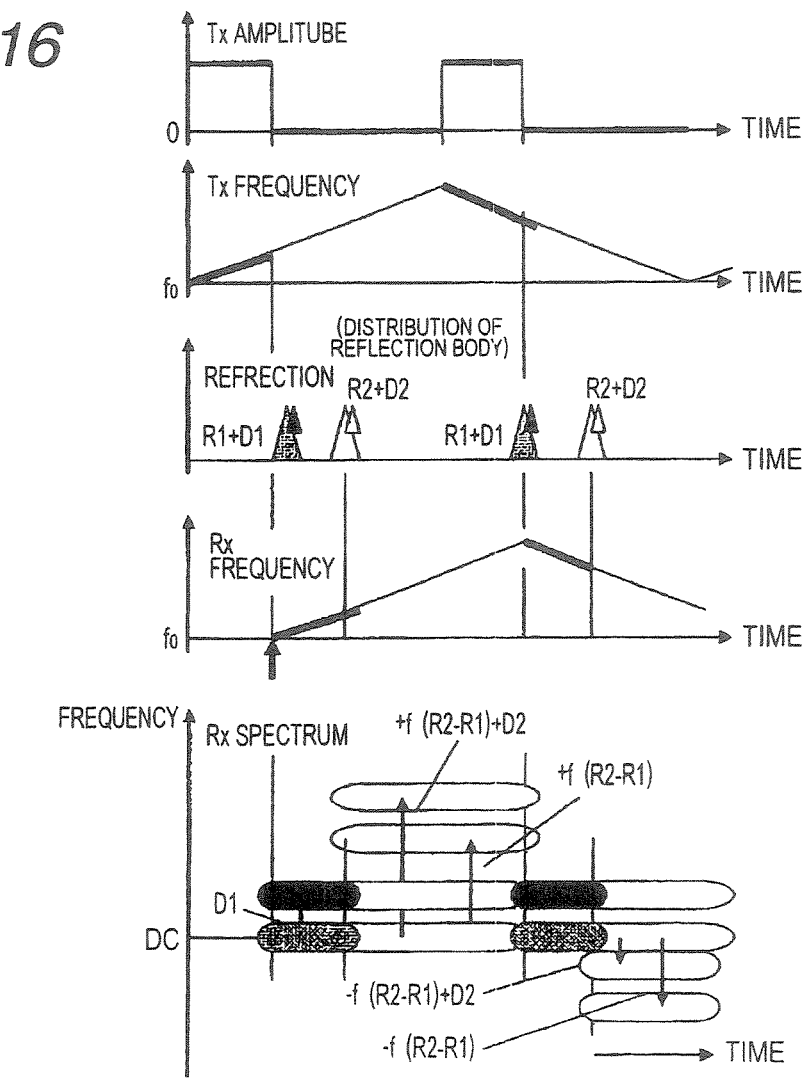

FIG. 17
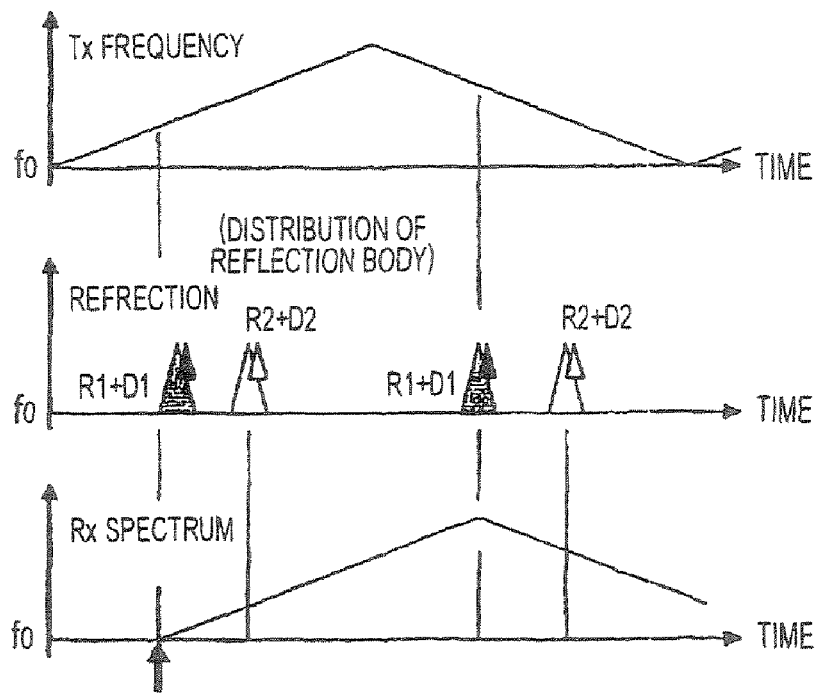
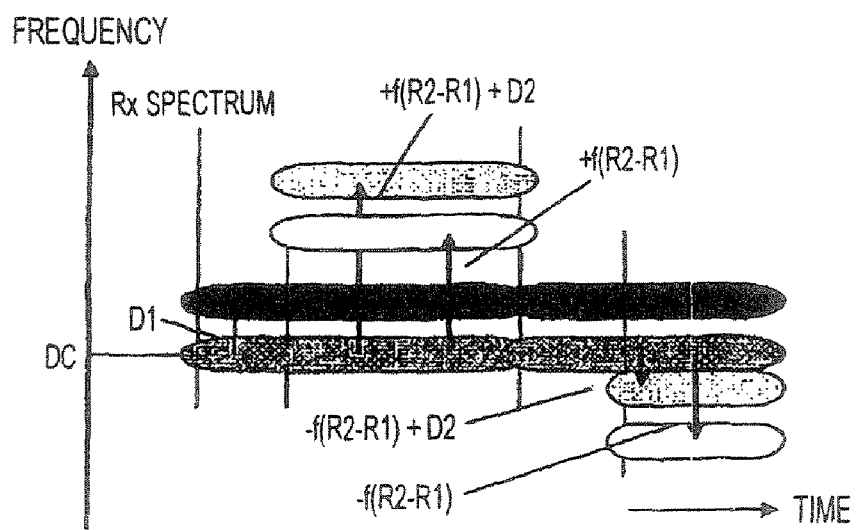

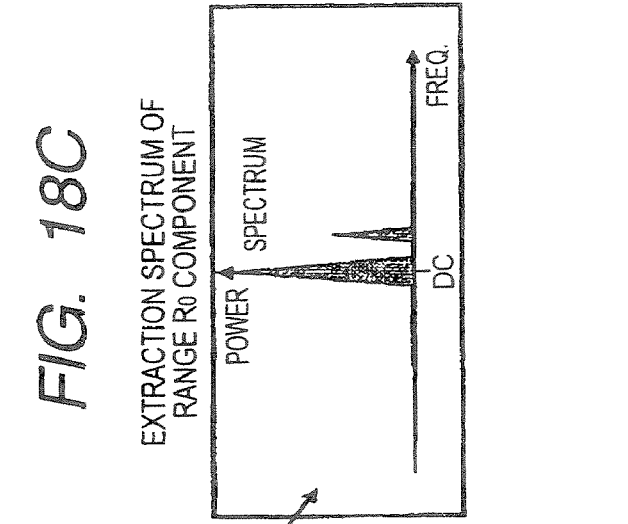
FIG. 18C
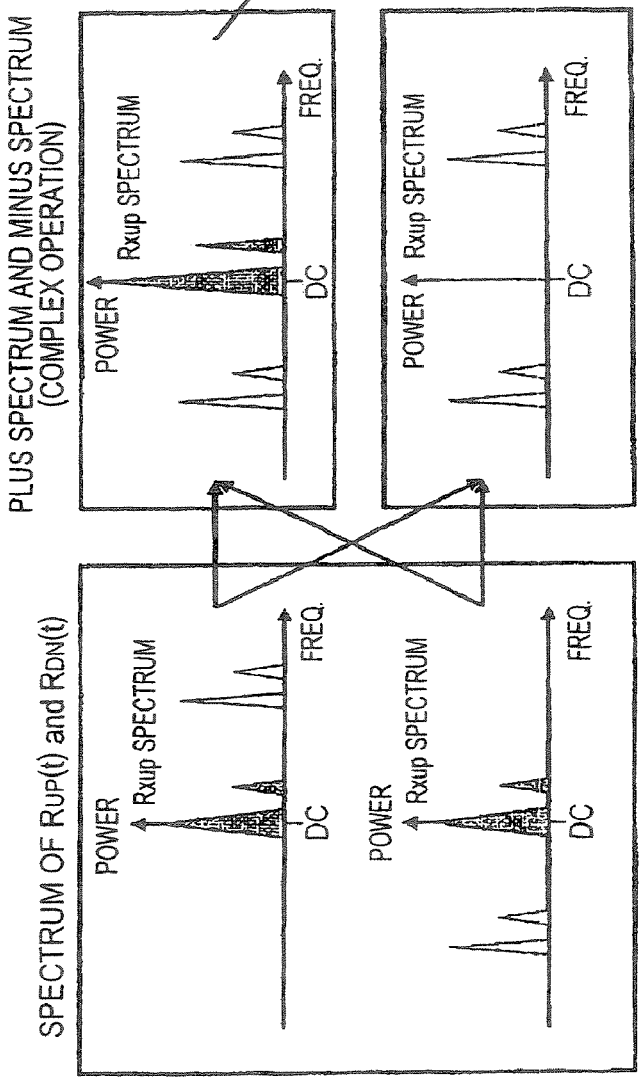
FIG. 18B
FIG. 18A

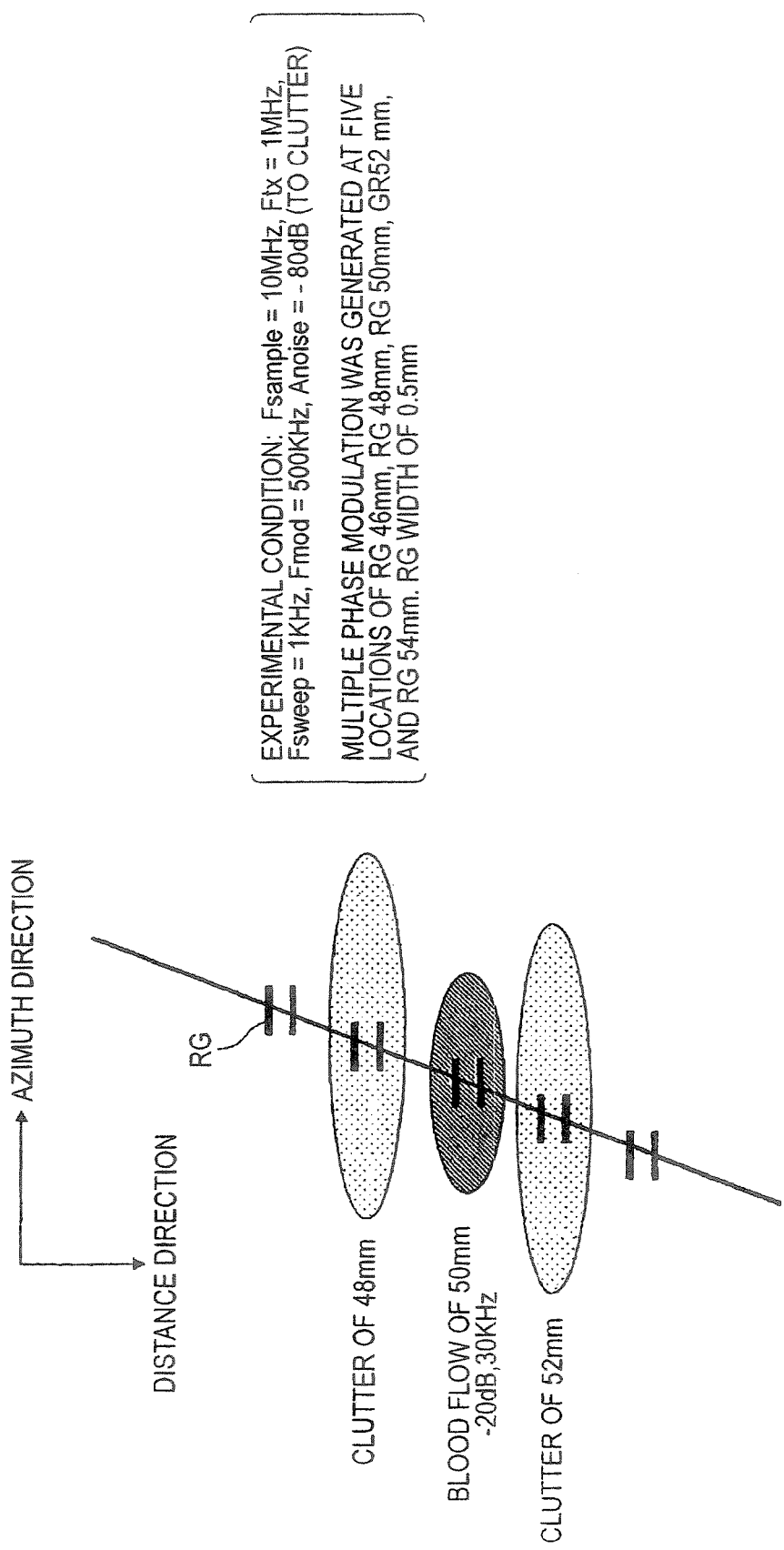

FIG. 21A

CROSS REGION PRESUMPTION
WAVEFORM IN AR MODEL
(THREE DIMENSION)

SOLID LINE : ACTUAL COMPONENT
BROKEN LINE : FALSE COMPONENT

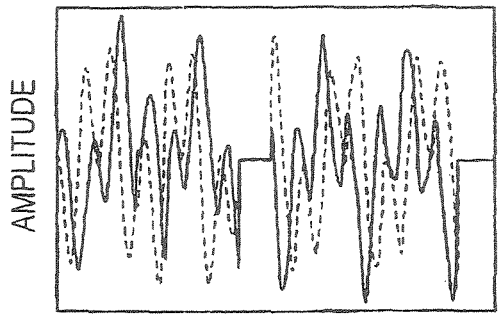

FIG. 21B

IQ WAVEFORM IN RG 46mm
(REMOVE CROSS REGION)

SOLID LINE : ACTUAL COMPONENT
BROKEN LINE : FALSE COMPONENT

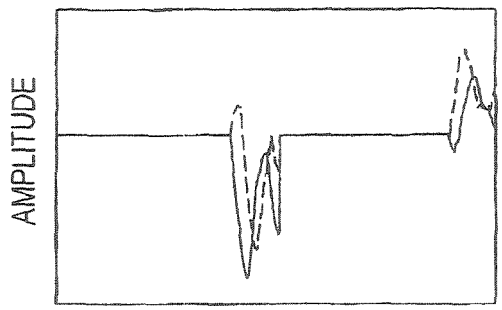

FIG. 21C

ADDING AND WEIGHTING OF IQ
SIGNAL AND PRESUMPTION SIGNAL

SOLID LINE : WEIGHTING OF IQ SIGNAL
BROKEN LINE : WEIGHTING OF
  PRESUMPTION SIGNAL

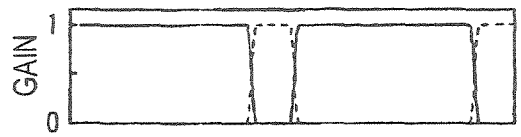

FIG. 21D

CONTINUOUS WAVEFORM
AFTER BLENDING

SOLID LINE : ACTUAL COMPONENT
BROKEN LINE : FALSE COMPONENT

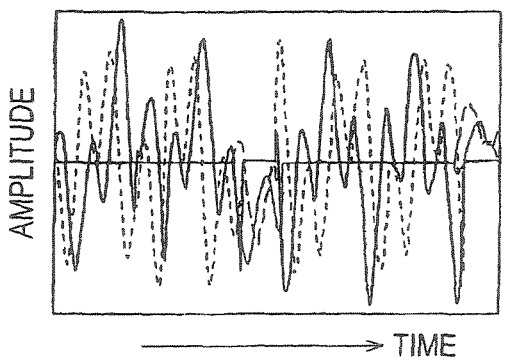

→ TIME
PAIR INTERVAL OF RISING
CHIRP/FALLING CHIRP

FIG. 22A

CROSS REGION PRESUMPTION
WAVEFORM IN AR MODEL
(THREE DIMENSION)

SOLID LINE : ACTUAL COMPONENT
BROKEN LINE : FALSE COMPONENT

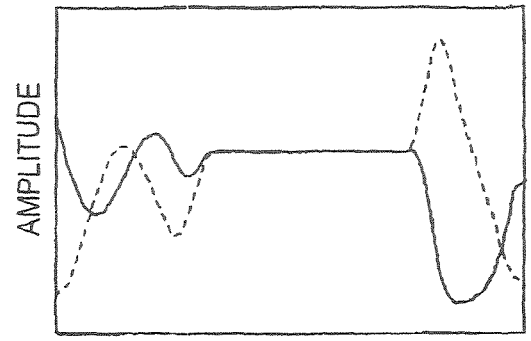

FIG. 22B

IQ WAVEFORM IN RG 46mm
(REMOVE CROSS REGION)

SOLID LINE : ACTUAL COMPONENT
BROKEN LINE : FALSE COMPONENT

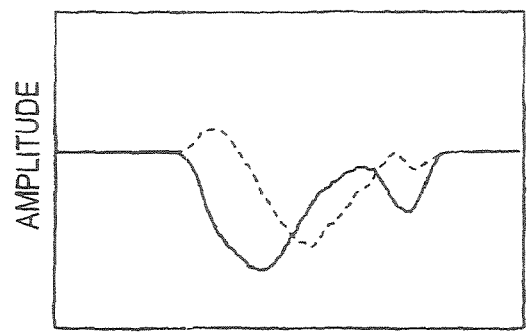

FIG. 22C

ADDING AND WEIGHTING OF IQ
SIGNAL AND PRESUMPTION SIGNAL

SOLID LINE : WEIGHTING OF IQ SIGNAL
BROKEN LINE : WEIGHTING OF
PRESUMPTION SIGNAL

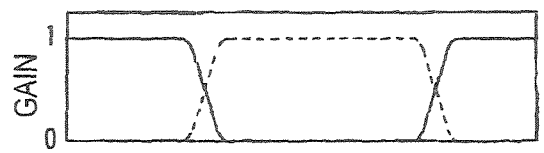

FIG. 22D

CONTINUOUS WAVEFORM
AFTER BLENDING

SOLID LINE : ACTUAL COMPONENT
BROKEN LINE : FALSE COMPONENT

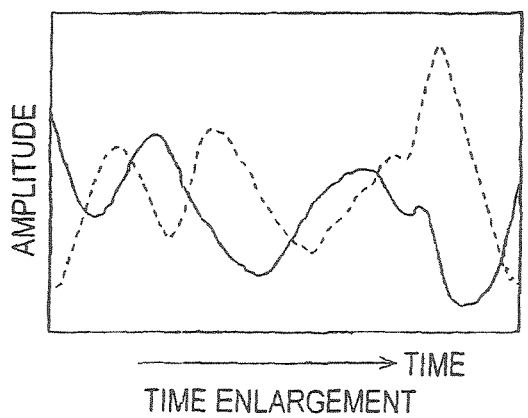

TIME ENLARGEMENT

FIG. 23A

CONTINUOUS TIME SERIES SIGNAL BY AR

FIG. 23B

HANNING WINDOW FUNCTION

FIG. 23C

RISING TIME SERIES AND FALLING TIME SERIES

SYNTHESIS PROCESS OF RISING COMPONENT AND FALLING COMPONENT

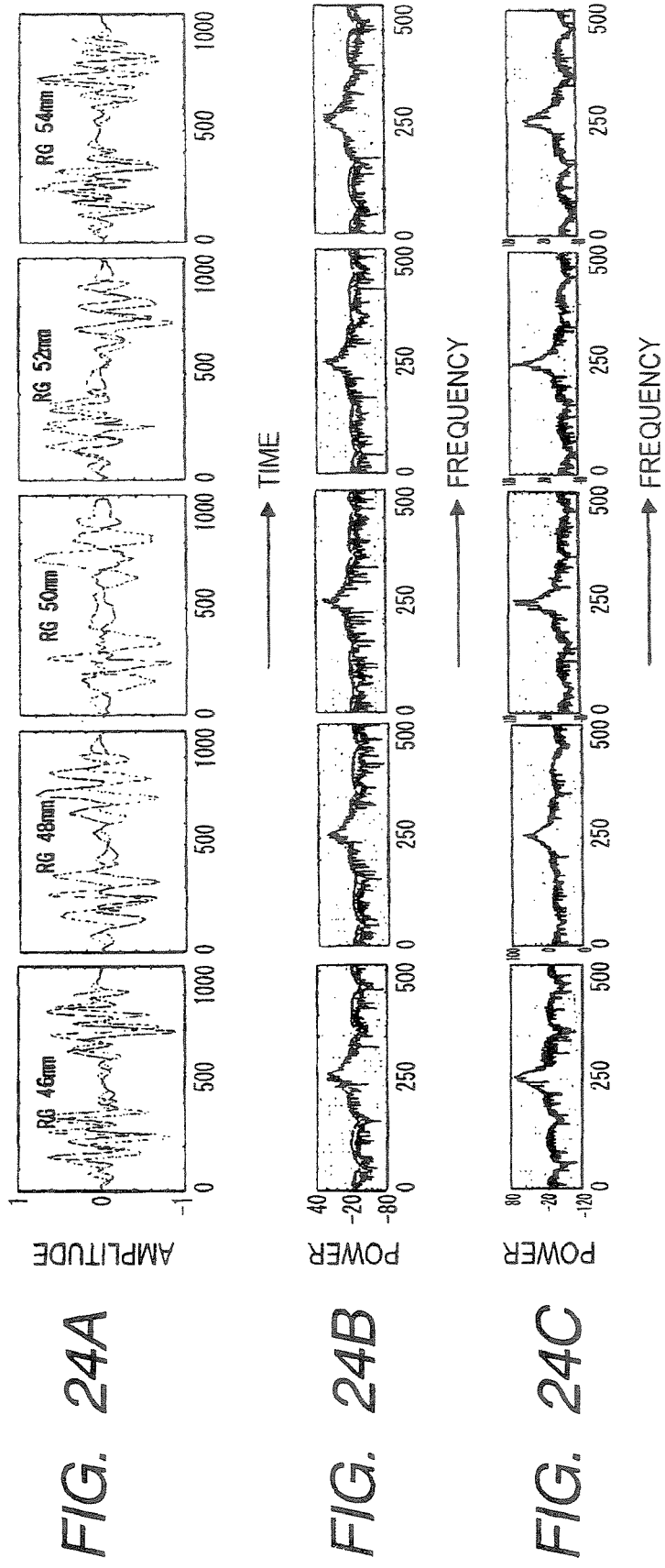

ON-RANGE SPECTRUM COMPONENT OF EACH RANGE / ENLARGED VIEW OF CENTER PORTION

FIXED MATERIAL POWER, MOVING MATERIAL POWER, AND MOVING MATERIAL AVERAGE SPEED IN EACH RANGE

CWM MODE DISPLAY IMAGE

ON-RANGE SPECTRUM COMPONENT
OF EACH RANGE

CONTINUOUS WAVE SYNTHESIZED IN
INVERSE FFT/SCALING PROCESS

CREATE CONTINUOUS WAVE COMPONENT BY
ADDING WHILE OVERLAPPING AFTER CUTTING
BY HANNING WINDOW

IQ SIGNAL OF CREATED CONTINUOUS WAVE

IQ SIGNAL CREATED BY WEIGHTING AND ADDING

IQ SIGNAL SPECTRUM OF CREATED
CONTINUOUS WAVE

SPECTRUM BEFORE PASSING
THROUGH WALL FILTER
( SPECTRUM AFTER WEIGHTING AND
ADDING THROUGH RG FUNCTION )

RGCW SPECTRUM IMAGE

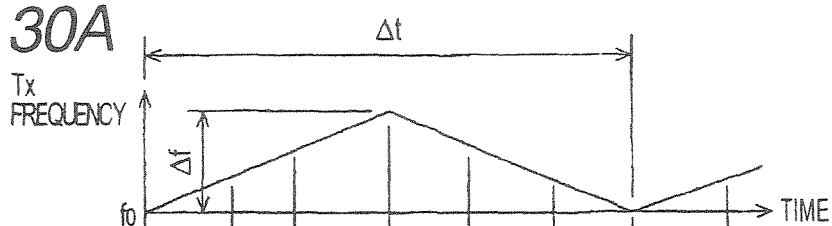
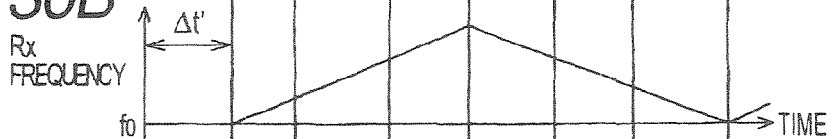
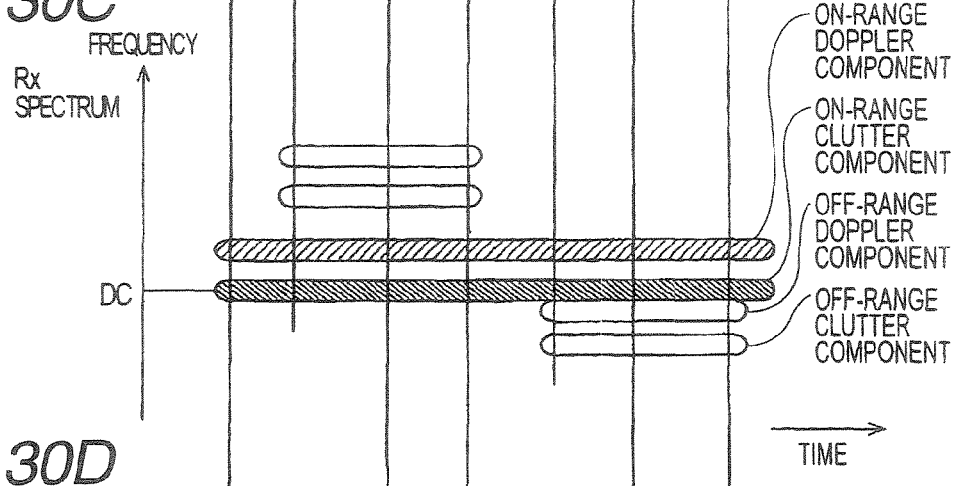
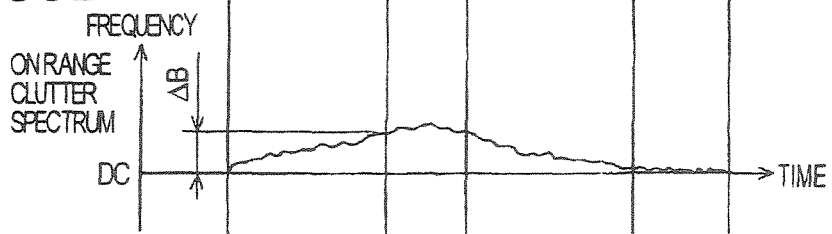

ULTRASONIC DOPPLER DIAGNOSIS DEVICE

TECHNICAL FIELD

The present invention relates to an ultrasonic wave Doppler diagnosis instrument. More particularly, the present invention relates to an ultrasonic wave Doppler diagnosis instrument which executes a continuous wave Doppler (CWD) using a continuous wave (CW) as an ultrasonic wave, and observes movement information of a blood flow that flows through a specific region of a distance direction with a resolution in the distance direction while making the most use of a merit in that there is no turnback due to the continuous wave Doppler.

BACKGROUND ART

An ultrasonic wave Doppler diagnosis instrument has become an indispensable modality at the time of observing a blood flow in a subject to be examined. In the ultrasonic wave Doppler diagnosis instrument, an X-ray exposure as in an X-ray diagnostic apparatus is not performed. A probe comes into contact with a body surface of the subject to be examined, so that the subject can be diagnosed. Therefore, it can meet a requirement for convenience in a medical field.

As an ultrasonic wave Doppler method which is performed by the ultrasonic wave Doppler diagnosis instrument, there are a pulsed wave Doppler (PWD) method and a continuous wave Doppler method (CWD). Of them, according to the pulsed wave Doppler method, using a pulsed wave as a transmission ultrasonic wave, only information of a blood flow of any specific depth can be detected. The pulsed wave Doppler method is mainly used in the heart or great arteries. However, in the pulsed wave Doppler method, since there is a restriction by a pulse repetition frequency (PRF), a so-called turnback phenomenon is generated. As a result, there is a restriction in a range of measurable blood flow speed.

In the meantime, according to the continuous wave Doppler method, a continuous wave is used as a transmitted ultrasonic wave. However, in processing a reflective ultrasonic wave signal where all Doppler signals in an ultrasonic beam direction overlap, there is a problem in that there is no distance resolution. In addition, since all reflective signals on a beam are collected, a clutter component of large power other than a Doppler component is contained. As a result, in obtaining sufficient Doppler sensitivity by using the continuous wave Doppler method, a large dynamic range or a steep wall filter is necessary. Therefore, the continuous wave Doppler method is mainly used for speed detection of a valve regurgitation jet of the heart or the like.

However, different from the pulsed wave Doppler method, the continuous wave Doppler method has a distinct advantage. That is, according to the advantage of the continuous wave Doppler method, the collection of blood flow information using a continuous wave can be made. Therefore, a Doppler range can be increased (specifically, a sampling frequency of a frequency analyzer is an upper limit), and a spectrum Doppler image can be obtained in which turnback does not occur even in a high-speed blood flow like a jet flow.

In the meantime, in a recent ultrasonic wave Doppler method, the needs have been required 'that want to detect fast blood flow deep within a subject to be examined without turnback'. These needs cannot be satisfied by the above-mentioned pulsed wave Doppler method and continuous wave Doppler method. Accordingly, some attempts have been made so as to meet these needs. One of some attempts is an HPRF (High PRF) method of a pulsed wave Doppler.

However, even though the HPRF method is used, it is likely for a second range gate to cause saturation in a short distance, and signals are not necessarily accurately collected from a deep portion of the subject.

In addition, another method for meeting the above-mentioned needs has been disclosed in Patent Documents 1 and 2. This method is based on a focus technology by a continuous wave Doppler method using an ultrasonic wave probe of a two-dimensional array. Specifically, according to this method, focus locations of transmission and reception are varied by means of not a conventional one-dimensional ultrasonic wave probe but a 1.5 dimensional or two-dimensional array-type ultrasonic wave probe having an array expanded in a lens direction (elevation direction), and a Doppler signal near the focus is selectively collected.

However, in the focus method disclosed in Patent Documents, the sensitivity near the focus is raised slightly, as compared with the sensitivity of a range other than the range near the focus. When a fixed material component/moving material component having large power exist on the same beam, it is not possible to obtain a sufficient distance resolution. In addition, since the detection is made with the sensitivity distribution that is determined by a sound field distribution of transmission and reception near the focus, a signal of a region having a large width may be detected, which results in not obtaining the sufficient distance resolution.

Patent Document 1: U.S. Pat. No. 2,500,937
Patent Document 2: U.S. Pat. No. 3,069,910

DISCLOSURE OF THE INVENTION

The present invention has been finalized in view of the drawbacks inherent in the conventional art, and it is an object of the invention to provide an ultrasonic wave Doppler diagnosis instrument which is capable of collecting blood flow information with high sensitivity without turnback from a blood flow that flows through a deeper part in a subject to be examined at a high speed.

In order to achieve the above-mentioned object, an aspect of the invention provides an ultrasonic wave Doppler diagnosis instrument which transmits an ultrasonic continuous wave in a range direction and receives a reflective wave of the ultrasonic continuous wave. The ultrasonic wave Doppler diagnosis instrument includes: a modulation unit that subjects the ultrasonic continuous wave to frequency modulation such that a phase is varied in accordance with the distance of the range direction; a demodulation unit that demodulates the reflective wave for each range of the range direction while interlocking with the frequency modulation, and generates a reception signal in the range in a separated state; and a presentation unit that presents information by using a signal of a Doppler component based on the reception signal.

According to the aspect of the invention, it is possible to collect blood flow information with high sensitivity without turnback from a blood flow that flows through a deeper part in a subject to be examined at a high speed.

BRIEF DESCRIPTION OF THE DRAWINGS

FIG. 7 is a diagram illustrating a discrimination algorithm of a signal component from clutter of an on-range and an off-range and a blood flow.

FIG. 14 is a diagram illustrating an outline of a process according to a first modification of the invention.

FIG. 15 is a diagram illustrating spectrums obtained in a (A) region of a chirp wave and a (D) region of a chirp wave in a range R3 shown in FIG. 14 and spectrums obtained by excluding a component of a fixed material from the corresponding spectrums.

FIG. 16 is a timing chart illustrating another modification.

FIG. 17 is a diagram illustrating a comparison example of FIG. 16.

FIG. 18 is a diagram illustrating a signal extraction process according to another modification.

FIG. 19 is a diagram illustrating a phantom model to which the simulation is applied and an experiment condition.

FIG. 21 is a graph illustrating a signal presumption process of a cross region in the simulation.

FIG. 22 is a temporal enlarged view of FIG. 21.

FIG. 23 is a graph illustrating a spectrum synthesis process in the simulation.

FIG. 24 is a diagram illustrating a synthesis signal in each range, a plus/minus component of a spectrum, and a spectrum component of an on-range.

FIG. 30 is a diagram illustrating a method of preventing a frequency resolution according to a condition of a chirp wave from being lowered.

BEST MODE FOR CARRYING OUT THE INVENTION

Hereinafter, the preferred embodiment of an ultrasonic wave Doppler diagnosis instrument of the invention will be described with reference to the accompanying drawings.

The ultrasonic wave Doppler diagnosis instrument provides a method of detecting a speed signal component of a moving material (blood flow or the like) that has a distance resolution by using a continuous wave as a transmission ultrasonic wave signal. The inventors called this method as 'a range gate CW (range gate continuous wave Doppler: RGCW) mode'. In the present embodiment, CW spectrum images, which are CWM (continuous wave motion) mode images and CW Doppler mode images, are supplied by using the range gate CW mode.

Figure 1:
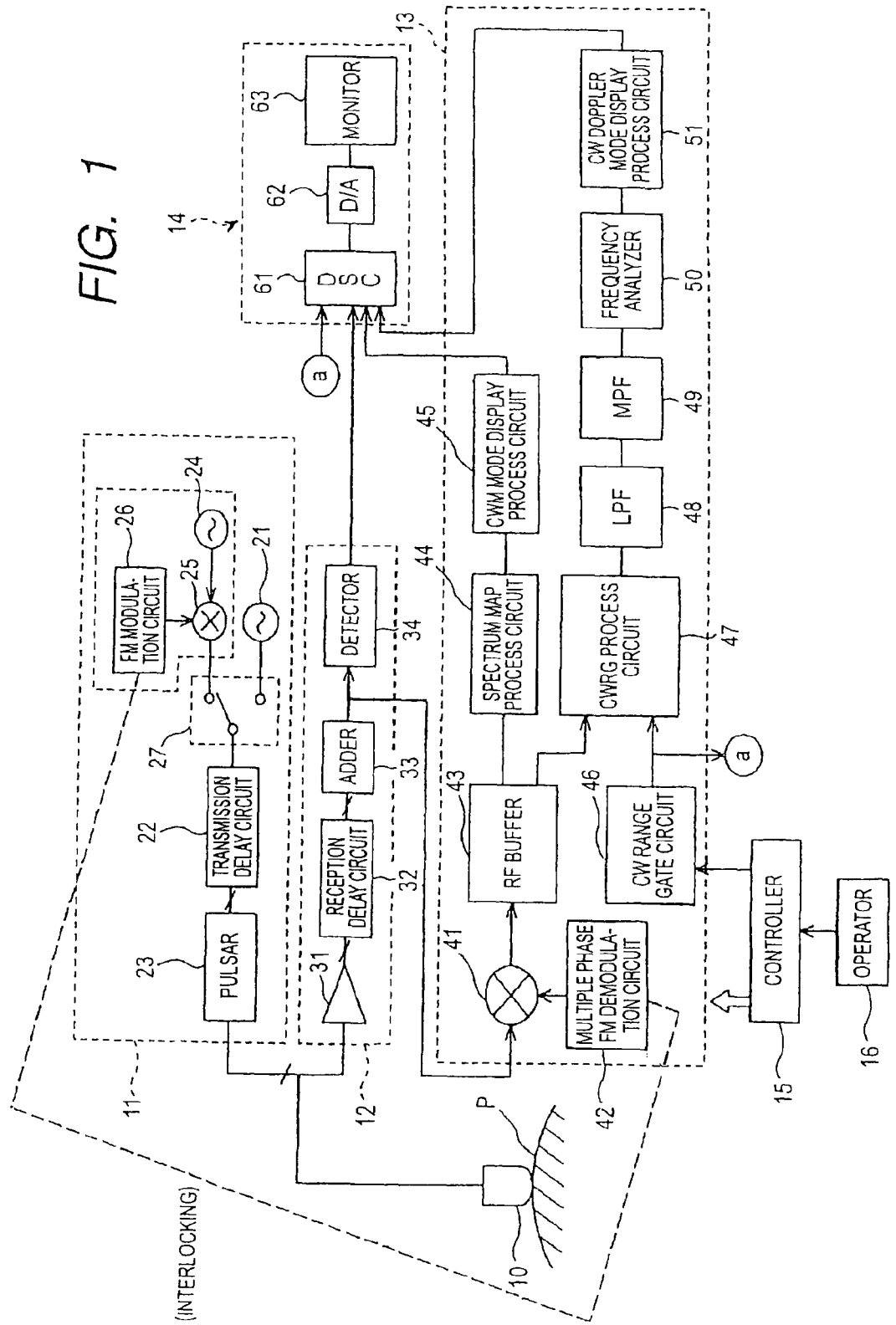
FIG. 1 is a block diagram schematically illustrating a structure of an ultrasonic wave Doppler diagnosis instrument according to a first embodiment of the invention.

As shown in FIG. 1, the ultrasonic wave Doppler diagnosis instrument includes a transmission block 11 that is connected to an ultrasonic wave probe 10, a B mode reception block 12, a range gate CW mode reception block 13, a display block 14 that is connected to both blocks 12 and 13, a controller 15, and an operator 16.

The ultrasonic wave probe 10 is composed of a one-dimensional block in which a plurality of piezoelectric vibrators for forming a plurality of channels are disposed in an array. The ultrasonic wave probe 10 generates an ultrasonic wave signal in response to a driving pulse for every channel that is supplied from the transmission block 11, and receives a reflection signal thereof so as to output a reception signal of an electrical amount from each piezoelectric element.

The transmission block 11 includes a transmission circuit for a B mode that has a pulse generator 21 for a B mode, a transmission delay circuit 22 that delays each transmission channel, and a pulsar 23 that generates a driving pulse, and a transmission circuit for a range gate CW mode that has a signal generator 24 for a range gate CW mode, a mixer 25, an FM (Frequency Modulation) modulation circuit 26, and a switch 27 that is inserted between the pulse generator 21 and the transmission delay circuit 22.

The signal generator 24 continuously oscillates a sine wave in order to transmit an ultrasonic continuous wave. The FM modulation circuit 26 raises a modulation frequency over a range of a predetermined sweep frequency, and then lowers the modulation frequency. Thereby, the FM modulation circuit 26 executes frequency modulation by a chirp wave in which a rising gradient and a falling gradient of a modulation frequency repeat. The mixer 25 mixes both output signals of the signal generator 24 and the FM modulation circuit 26 so as to output the mixed signal.

The switch 27 can selectively switch a path into the pulse generator 21 for a B mode and the mixer 25 for a range gate CW mode in response to a switching control signal from the controller 15.

The B mode reception block 12 includes a preamplifier 31 provided for each reception channel, a reception delay circuit 32 that performs a reception delay for each reception channel so as to perform a phasing adding process, an adder 33 that adds a delay-controlled reception signal of each reception channel, and a detector 34 that performs envelope detection. Thereby, a B mode signal, which is located at each sample point on a raster, is obtained from the detector, and then transmitted to the display block 14.

The range gate CW mode reception block 13 collects the range gate CW mode image according to the present embodiment together with the above-mentioned transmission circuits (24, 25, and 26) for a range gate CW mode. As shown in FIG. 1, the reception block 13 includes, as common circuits, a mixer 41, a multiple phase FM demodulation circuit 42 that performs a phase shift to perform demodulation, and a RF (Radio Frequency) buffer 43. In addition, the reception block 13 includes a circuit group for a CWM mode and a circuit group for a CW Doppler mode.

Of them, the circuit group for a CWM mode includes a spectrum buffer process circuit 44 that is connected to a RF buffer 43, and a CWM mode display process circuit 45 that is connected to the process circuit 44. The image data of the CWM mode, which is processed by the display process circuit 45, is transmitted to the display block 14. In addition, the circuit group for a CW Doppler mode includes a CW range gate circuit 46 that generates a range gate, a CWRG process circuit 47 that is connected to the gate circuit 46 and the RF buffer 43, an LPF 48 (Low Pass Filter), an HPF 49 (High Pass Filter), a frequency analyzer 50, and a CW Doppler mode display process circuit 51. The CW spectrum image data, which is processed by the display process circuit 51, is transmitted to the display block 14. In addition, a process and operation by the range gate CW mode reception block 13 is described in detail below.

The display block 14 includes a digital scan converter (DSC) 61 that receives image data from the B mode process block 12 and the range gate CW mode reception block 13, a D/A (Digital to Analog) converter 62, and a display monitor 63. The DSC 61 performs A/D (Analog to Digital) conversion on the B mode image signal that is transmitted as an analog amount, and executes scan conversion so as to create image data for display.

The controller 15 controls the operation timing of an entire instrument or a display mode in accordance with a program according to a predetermined algorithm stored in advance as well as operation information of a user supplied through the operator 16.

Hereinafter, a process and operation by the range gate CW mode reception block 13 are mainly described.

Figure 2:
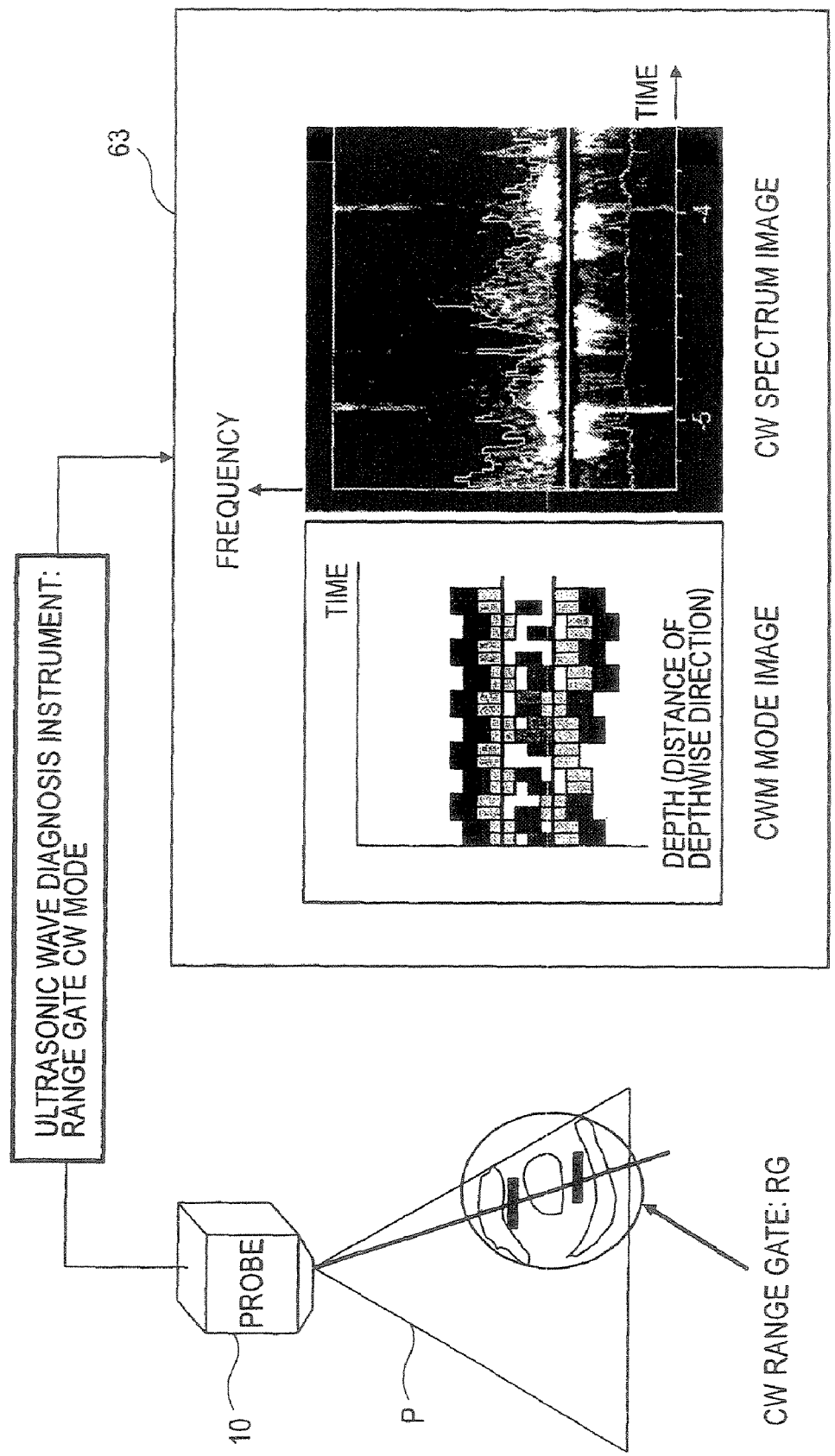
FIG. 2 is a diagram illustrating an outline of a range gate CW mode performed in the ultrasonic wave Doppler diagnosis instrument according to the first embodiment of the invention.

As shown in FIG. 2, the ultrasonic wave Doppler diagnosis instrument according to the present embodiment can display CW spectrum images serving as a CWM mode image and a CW Doppler image from a reflective wave of an ultrasonic continuous wave that is received through the ultrasonic probe 10 and subjected to frequency modulation. The CWM mode image is a distribution diagram that shows a range (depth of a raster direction) in a longitudinal axis and time in a horizontal axis by applying gradations of white and black to a signal of a fixed material component that is obtained for each range of a range direction along each raster (scanning line) and applying a color to a signal of a moving material component. In addition, the CW spectrum image is a distribution diagram that shows a power spectrum of a Doppler component (in a state where a frequency is shown in a longitudinal axis and time is shown in a horizontal axis) by extracting a Doppler component of a range corresponding to a predetermined range gate (CW range gate) set on a B mode tomographic image and performing weight addition on the Doppler component.

Signal Process of Transmission and Reception

Figure 3:
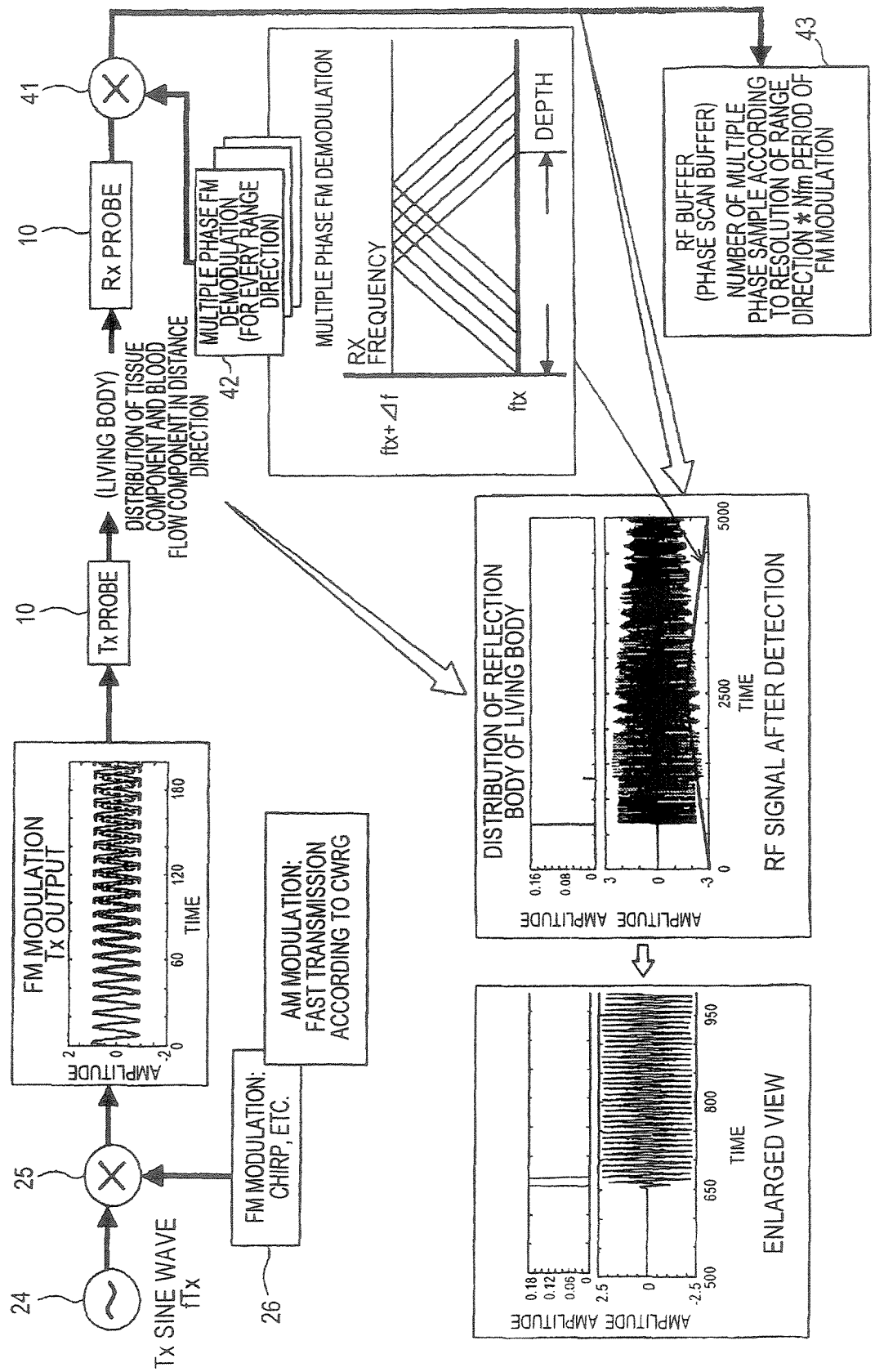
FIG. 3 is a diagram schematically illustrating a transmission/reception signal process performed in the ultrasonic wave Doppler diagnosis instrument according to the first embodiment of the invention.

FIG. 3 shows an outline of a signal process block that is constructed by a transmission circuit for a range gate CW mode mounted on the transmission block 11 and the range gate CW mode reception block 13.

The signal process block forms a circuit group in order to extract, separately from each other, four kinds of signal components that includes signal components of a clutter (fixed material)/blood flow (moving material) where a distance is equal in each range (RG) of a range direction and signal components of a clutter/blood flow where a distance is not equal in each range (RG) of a range direction, from a received reflective wave signal.

The sine wave, which is generated by the signal generator 24, is subjected to frequency modulation based on the chirp wave by the FM modulation circuit 26 and the mixer 25, and is then transmitted along each raster to the inside of a subject P as an ultrasonic continuous wave through the ultrasonic wave probe 10. The ultrasonic reflective wave, which is reflected from a tissue component or a blood flow component of the subject P, is received by the ultrasonic wave probe 10, and is transmitted, modulated, and interlocked by the mixer 41 and the multiple phase FM demodulation circuit 42 for every range direction. Then, the ultrasonic reflective wave is subjected to the multiple phase FM demodulation. The interlocking means that the FM demodulation is performed by the chirp wave synchronized with the chirp wave for frequency modulation with respect to the transmission continuous wave at a predetermined time interval. The multiple phases mean that the phases of the transmission modulation and the reception modulation are varied for each range of a range direction (beam direction).

The detection signal, which is obtained by the demodulation, is stored as digital data by means of an A/D converter (not shown) of the RF buffer 43. This RF buffer 43 serves as a phase scan buffer. As the detection signal is stored, the sample data of the multiple phases according to the resolution of the range direction is mapped by an Nfm period of FM modulation.

Figure 4:
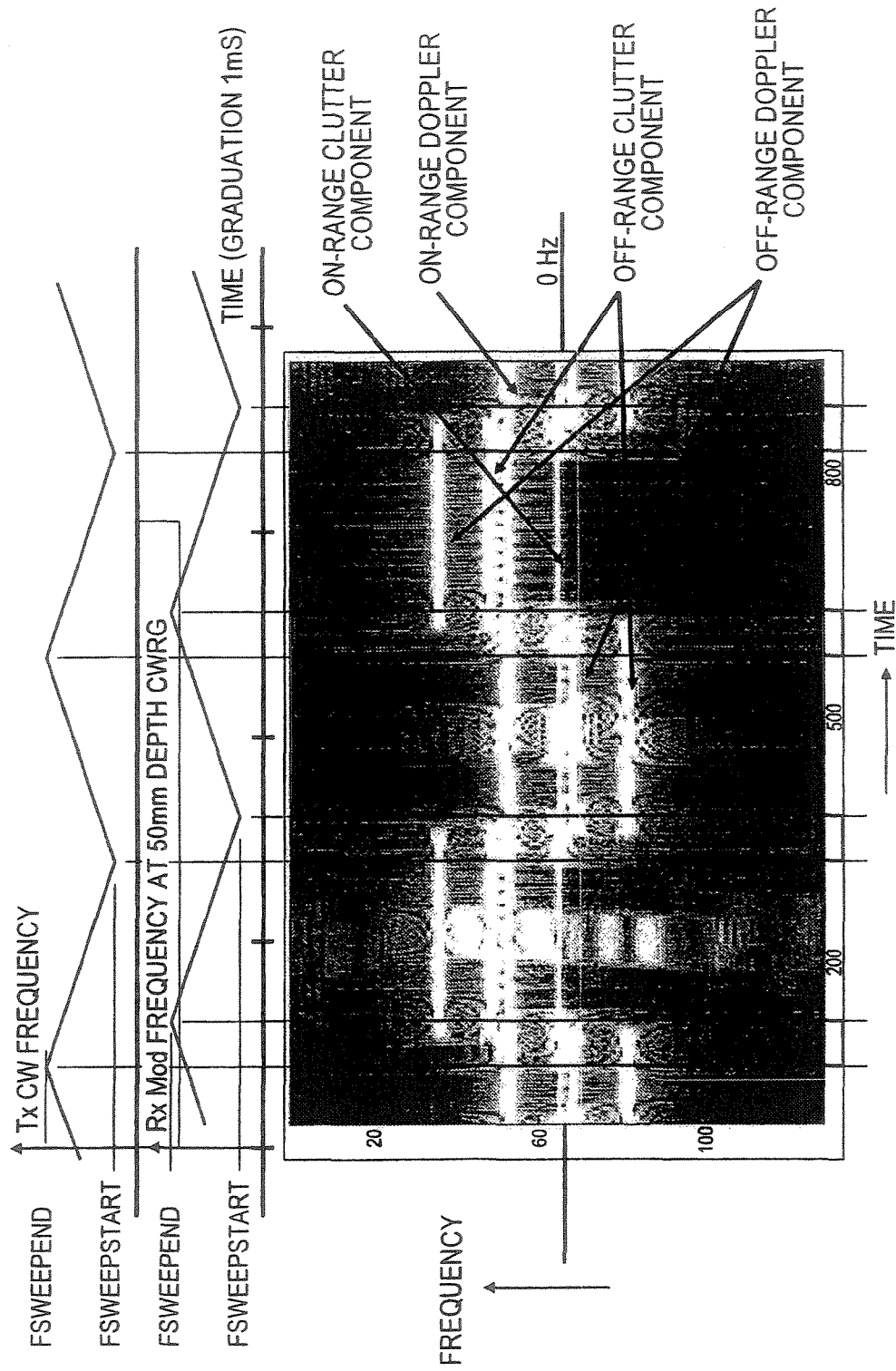
FIG. 4 is a diagram illustrating a spectrum of a demodulation signal.

In this case, FIG. 4 illustrates a spectrum of a signal demodulated by the multiple phase demodulation. The multiple phase demodulation method corresponds to a demodulation method in which phases of the transmission modulation and the reception modulation are varied for every range. For this reason, as can be understood from the spectrum shown in FIG. 4, the frequency modulation at the time of transmission and the multiple phase FM demodulation at the time of reception are interlocked at a predetermined time interval. In the signal which is obtained after performing the multiple phase FM demodulation, a signal component of a clutter and a blood flow (Doppler) component of (an on-range) where the distance is the same in each range, a signal component of a clutter and a blood flow (Doppler) component of (an off-range) where the distance is not the same in each range, and a signal component of a cross region are mixed. The cross region refers to a time zone when the modulation gradient of the frequency at the time of transmission modulation and the modulation gradient of the frequency at the time of reception demodulation are opposite to each other in a polarity (rising gradient and falling gradient).

As can be understood from a spectrum of a lower stage of FIG. 4, the signal component of the clutter of the on-range becomes a DC (Direct Current) component, but the signal component of the blood flow (Doppler) of the on-range becomes a continuous wave by deviating at one polarity side by a predetermined offset. In the meantime, the signal component of the clutter of the off-range is divided so as to have symmetry with respect to both polarities, but the signal component of the blood flow (Doppler) of the off-range is divided so as to have asymmetry with respect to both polarities.

As such, according to the multiple phase FM demodulation, an appearance of a signal component on the spectrum component is different depending on whether a corresponding range is an on-range for every range and whether it is a signal component from the blood flow (Doppler). Therefore, by using the difference between the appearances, a signal component can be extracted from the clutter of the on-range and the blood flow.

In the cross region, various artifacts are mixed, but they are not used in the display process of the image data.

Figure 5A:
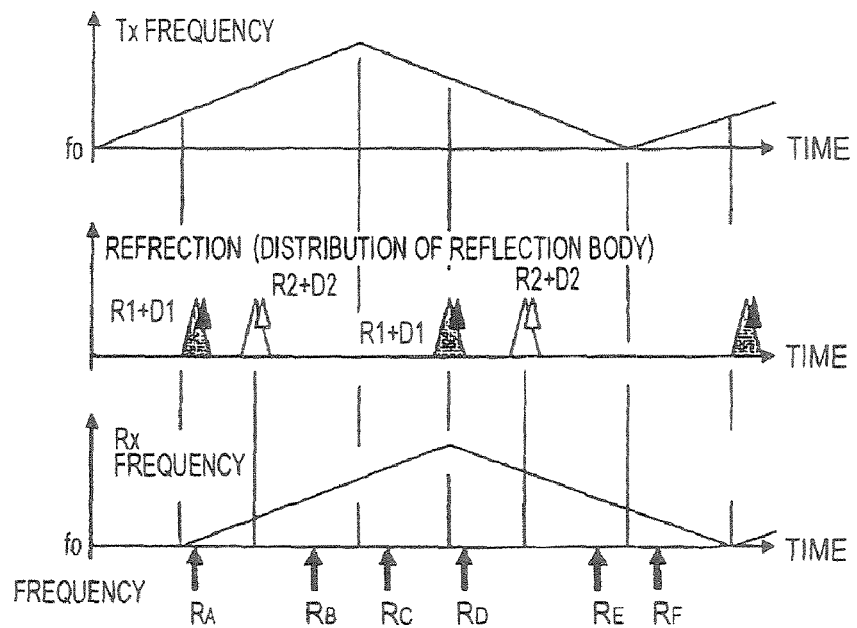
FIG. 5 is a diagram illustrating six regions of a time variation of a spectrum.
Figure 5B:
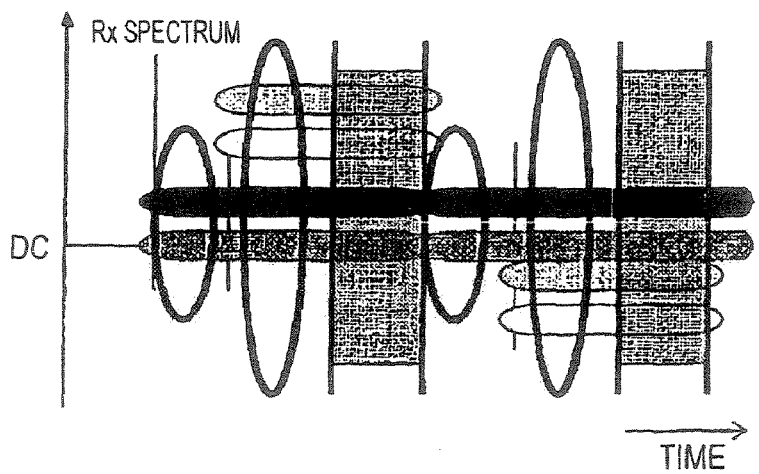

An explanatory view of FIG. 4 is shown in FIGS. 5 and 6. In the signal detected by the multiple phase FM demodulation method, with respect to a complementary pair which is composed of a chirp wave of the rising gradient and a chirp wave of the falling gradient, the time variation of the spectrums of the signal component R1+D1 (fixed material component+moving material component) of the on-range and the signal component R2+D2 (fixed material component+moving material component) of the off-range can be classified into six regions ($R_A$ to $R_F$) shown in FIG. 5.

Figure 6A:
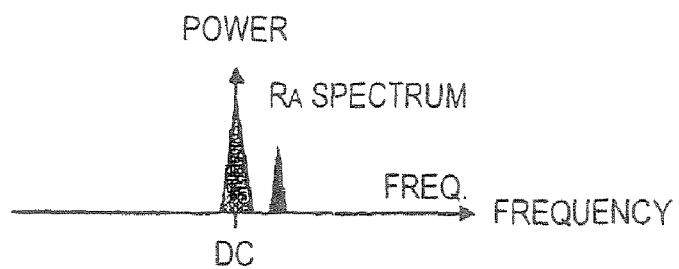
FIG. 6 is a diagram illustrating a relationship between a chirp frequency location of Rx demodulation and a spectrum.
Figure 6B:
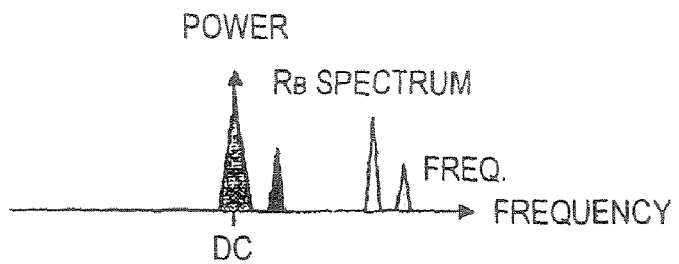
Figure 6C:
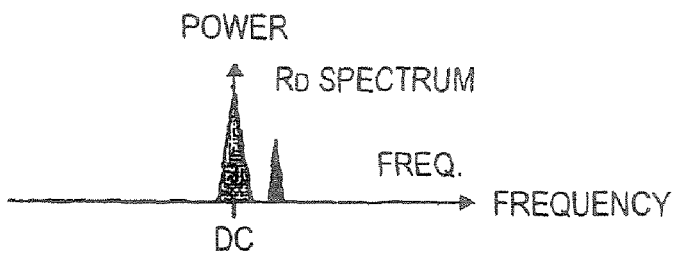
Figure 6D:
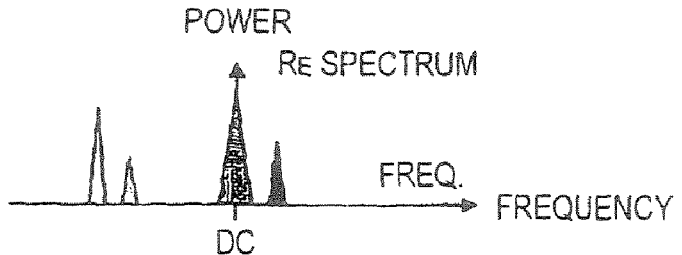

That is, as shown in FIG. 6, in the $R_A$ (FIG. 6(A)) and the $R_D$ (FIG. 6(C)) near the minimal frequency of the chirp wave of the rising gradient and the maximum frequency of the chirp wave of the falling gradient, the Doppler component and the fixed material component of the on-range R1 do not exist. The on-range R1 component becomes a continuous spectrum.

In the CW spectrum image in the range gate CW mode, only the Doppler component of the on-range R1 (substantially a single frequency component when a range interval is small) is necessary. Therefore, the center frequency/variation of the spectrum, which is obtained by removing (HPF) a DC component on the basis of the spectrums of the regions of $R_A$ and $R_D$, is calculated, and the BPF (Band Pass Filter) process is performed on a time base according to the center frequency/variation of the spectrum. As a result, the continuous component may be extracted.

In the regions of $R_C$ and $R_F$ where the transmission continuous wave Tx and the reception wave RX thereof are opposite to each other in a polarity of the frequency modulation (referred to as cross regions), a plurality of spectrum components are mixed with each other so as to form an artifact, but the artifact is not used in presuming the spectrum.

Discrimination Algorithm of Signal Component

In order to extract the on-range component from the signal detected by the above-mentioned multiple phase FM demodulation method, the discrimination algorithm shown in FIG. 7 is applied. Specifically, a complex spectrum of the rising gradient chirp wave signal and the falling gradient wave signal is calculated, except for the cross region (FIG. 7(A)), and the absolute values of the spectrums of the plus component/minus component are calculated (FIG. 7(B)). Next, the difference between the absolute values of the spectrums of the plus component/minus component is calculated (FIG. 7(A)). Thereby, it is possible to discriminate the fixed material component (clutter) and the moving material component (Doppler) of the on-range.

Further, a band filter (HPF and LPF) is applied to the extracted signal, that is, a signal, excluding the signal component of the off-range becoming the artifact (FIG. 7(D)), and it is separated into the fixed material component and the moving material component of the on-range (FIG. 7(E)).

Width Control and Process of Cross Region

Figure 8:
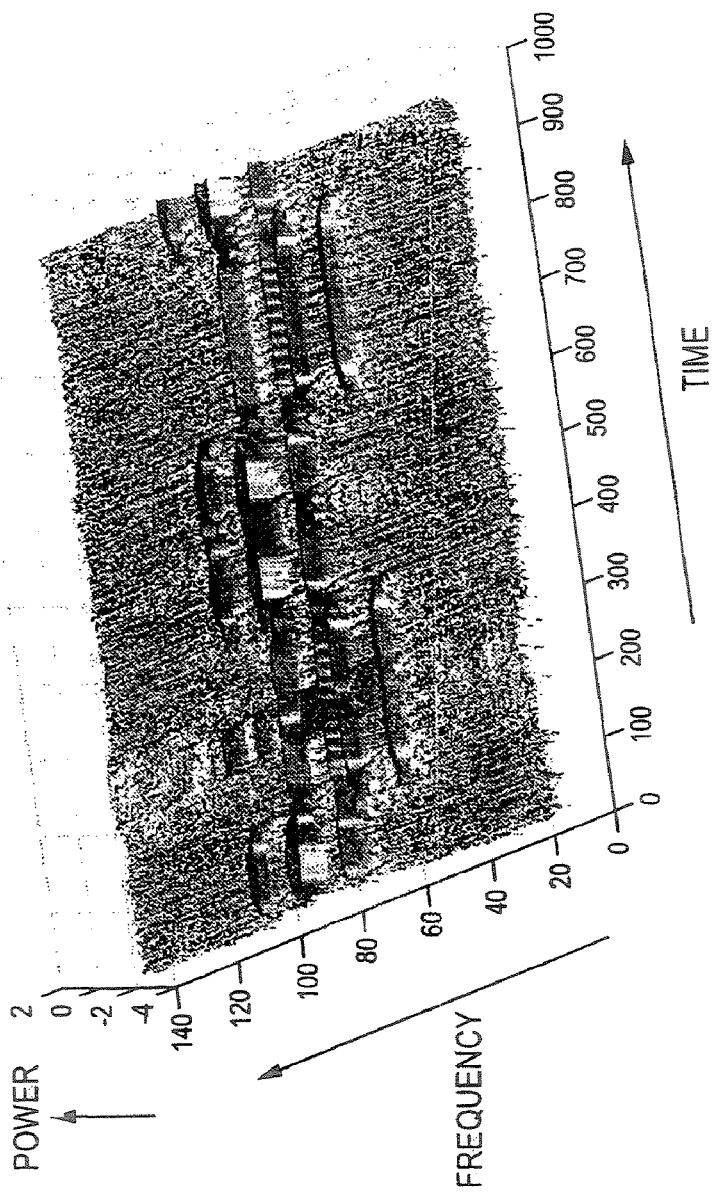
FIG. 8 is a simulation view illustrating occurrence of a cross region.

As described above, since the artifact is included in the cross region, the signal of the cross region is removed without being used at the time of analyzing the spectrum. For this reason, preferably, the width of the cross region (time width) is controlled so as to be as small as possible. In the present embodiment, the multiple phase FM modulation (where FMCW (frequency modulation) parameter: sampling frequency fsample=10 MHz, sweep start frequency fsweepstart=1 MHz, sweep end frequency fsweepend=1.5 MHz, sweep frequency Δf (=fsweepend−fsweepstart=)=500 kHz, modulation frequency fmod=500 Hz, 128 point FFT, fscaling=1 MHz, CWRG=50 mm Depth) is performed on a model in which a clutter component and a Doppler component of 30 KHz exist in each of Depth=50 mm and Depth=100 mm. As a result, the result shown in FIG. 8 is obtained. From this result, it can be understood that the width where the cross region is generated depends on the depth of the CWRG (range of a distance direction), and a frequency of Fmod (reciprocal number of a modulation period of a chirp wave). For this reason, in order to reduce the cross region, the Fmod frequency may by lowered or the CWRG position may be lowered.

Figure 9:
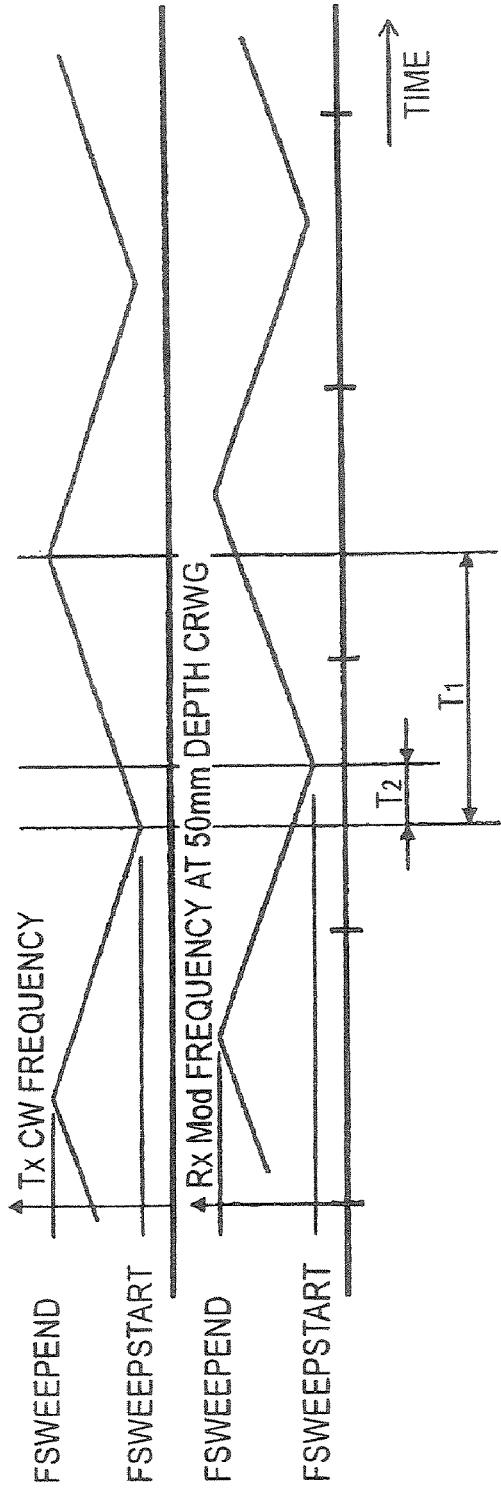
FIG. 9 is a diagram illustrating control of a width of a cross region.

Here, if considering the ratio of the cross region from the chart illustrated in FIG. 9, it is as follows.

$$T1 = 1/(2 * fmod)$$

$$T2 = 2 * CWRGposition/C \quad \text{[Equation 1]}$$

(In this case, actually, since the CWM mode exists, the position CWRGposition of CWRG corresponds to the depth, that is, the position CWRGposition of CWRG=Depth). Therefore, the ratio of the cross region is represented as T2/T1. As described above, the signal of the cross region, is removed. Instead of the signal from the cross region, a signal extrapolated in the MSE (missing signal estimation) is created. For this reason, in order to easily and surely perform this extrapolation, the width of the cross region is preferably controlled such that the ratio T2/T1 (ratio of the cross region) becomes a value less than a predetermined value (for example, a value less than 30%).

Figure 10A:
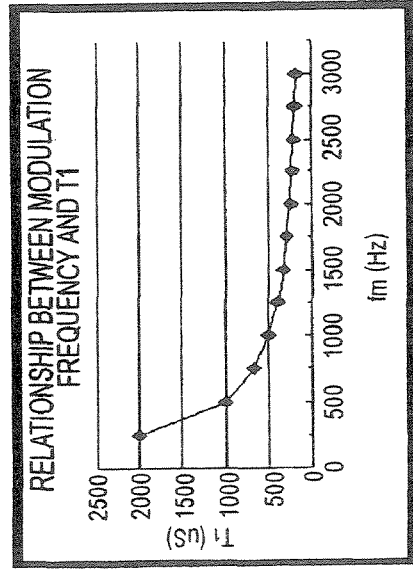
FIG. 10 is a diagram illustrating a restriction and control type of a cross region.
Figure 10B:
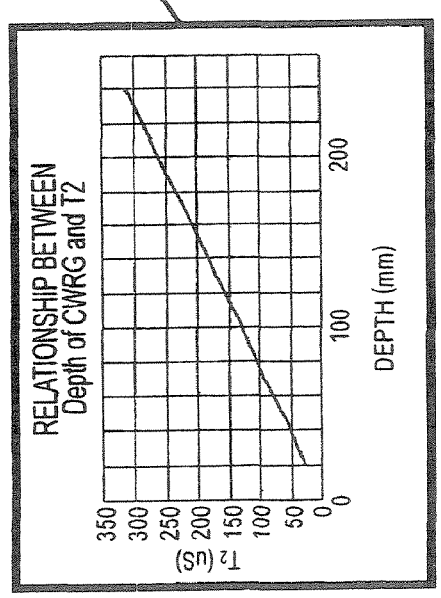

Actually, as shown in FIG. 10, the time T1 is in inverse proportion to the modulation frequency fm (FIG. 10(A)), and the time T2 is in direction proportion to the Depth (FIG. 10(B)). An effective region, which can be used in analyzing a remaining spectrum (frequency), excluding the cross region, is as follows.

$$\text{Valid}(\%) = 100 * (T1 - T2)/T1 \quad \text{[Equation 2]}$$

Figure 10C:
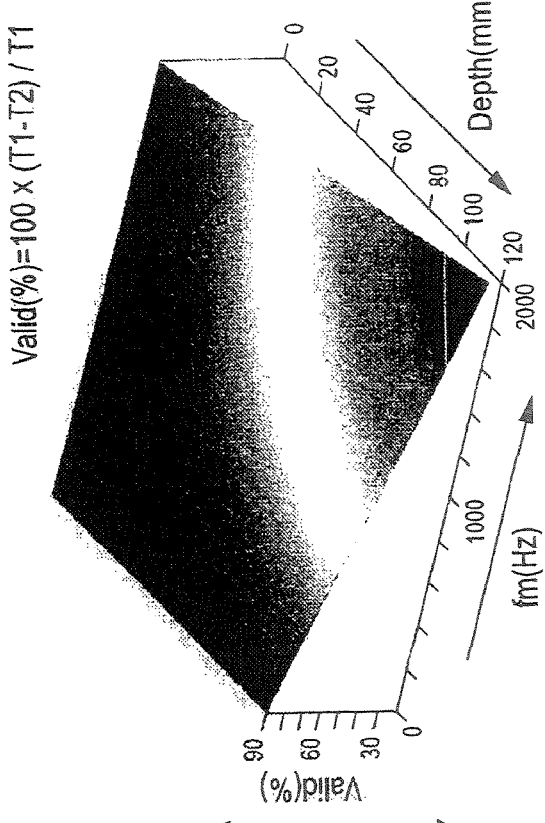

From the equation 2, the effective region Valid is represented as contour lines indicating the modulation frequency and the Depth (FIG. 10(C)). For this reason, when the width of the cross region is controlled, the modulation frequency is automatically controlled in accordance with the location of the CWRG such that the above-mentioned effective region Valid obtains, for example, 80% or more.

Subsequently, the control of the frequency resolution and the time resolution of each range direction will be described. In order to increase the frequency resolution, the observation time T1−T2 may be increased. In this case, the modulation frequency fmod may be lowered, but time resolution may be lowered as much as the lowered modulation frequency. In the meantime, in order to increase the time resolution, the inclination of Δf/Δt may be increased. In this case, the sweep frequency needs to be raised, but since the beat frequency of the clutter becomes raised as much as the raised sweep frequency, the sampling frequency should be raised. For this reason, a common ground between the frequency resolution and the time resolution is searched, or the resolution control is performed such that any one of the frequency resolution and the time resolution has priority.

In a case of spectrum display, since the maximum range of the display and the frequency resolution are determined in accordance with the observation time length and the sampling frequency of the frequency analyzer, the scaling or resampling is performed by dropping the signal band, and thus the observation time length and the sampling frequency can be varied.

Figure 11:
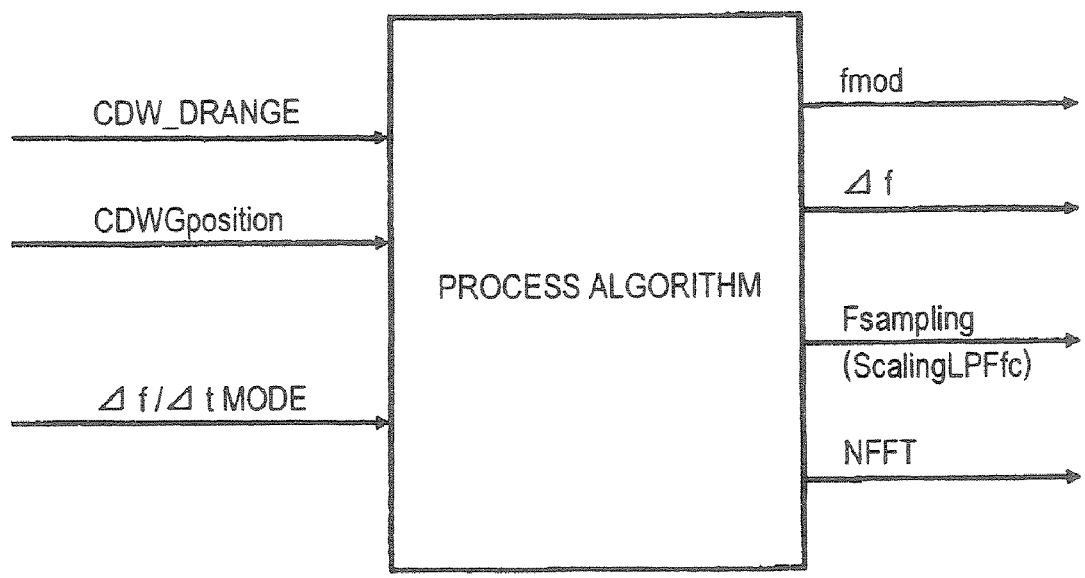
FIG. 11 is a diagram illustrating an input/output parameter for controlling a time resolution and a frequency resolution.

If the above is collected as the method of controlling the time resolution and the frequency resolution, the process algorithm is made by using each parameter shown in FIG. 11. That is, (1): the sampling frequency Fsampling, which covers the beat range of the clutter+the maximum Doppler range from the CWRGposition (corresponding to Depth), and the cut off of the ScalingLPF of the pretreatment are calculated. Next, (2): fmod and Δf are calculated in accordance with the restriction of the sample range while depending on any mode of the time resolution priority mode and the frequency resolution priority mode. Next, (3): the sampling frequency is calculated from the above-mentioned maximum range, the observation time is calculated from the minimum range, and the number of FFT (Fast Fourier Transform) of a frequency analyzer according to the sampling frequency and the observation time is calculated.

As such, in the cross region, since the chirp wave of the transmission modulation and the chirp wave of the reception demodulation are different from each other in the polarity of the modulation frequency, various spectrum components are mixed so as to form the artifact. If the artifact is used as it is, the spectrum presumption precision of the rear stage is deteriorated. Accordingly, the cross region is removed. Instead of it, the signal component presumed from the time series signal or the spectrum of the sequence is inserted. In particular, in the case of the range gate CW (RGCW) mode display according to the present embodiment, the spectrum analysis is performed while using the continuous wave as the base. Therefore, the continuous wave is generated by extrapolating and synthesizing the continuous time series signal component.

Hereinafter, two kinds of specified examples where the signal is extrapolated will be described. In a first example, the time series signal is used. Using the time series signal, except for the cross region, using an AR (Auto Regressive) mathematical model (or referred to a statistical model) from the observation region before and after the missed region, using the system-identified parameter, and on the basis of the signal source, such as a noise or the like, the signal of the missed interval is predicted. At this time, the signal presumption may be made even during any case of when the signal presumption is made from the past data in a forward direction, when the signal presumption is made from the future data in a reverse direction, and when the signal presumption is made for both the forward direction and the reverse direction. In addition, in order to maintain the continuity of the signal, the missed portion and the original signal portion overlap each other to be then subjected to weighting, such as a window function or the like, and adding, and the continuous signal is synthesized. In addition, in the present embodiment, as a signal extrapolating method of the cross region, a method using the time series signal is used.

In a second example, the spectrums of the pair of the rising gradient and the falling gradient, except for the cross region, are used. Using the AR-identified parameter from the observation region before and after the missed region by the cross region, the spectrum of the missed interval is presumed. At this time, the spectrum of the missed interval may be presumed even during any case of when the spectrum of the missed interval is presumed from the past data in a forward direction, when the spectrum of the missed interval is presumed from the future data in a reverse direction, and when the spectrum of the missed interval is presumed for both the forward direction and the reverse direction. In addition, in order to maintain the continuity of the time variation of the spectrum, the missed portion and the original spectrum overlap each other to be then subjected to weighting, such as a window function or the like, and adding, and the continuous spectrum is synthesized. The synthesized spectrum is subjected to an inversed Fourier transform so as to generate the continuous time series signal.

Process of CWM Mode and Display

Next, the process, which is performed by the spectrum map process circuit 44 and the CWM mode display process circuit 45, will be described with reference to FIG. 12. In the RF buffer 43 which serves as a phase scan buffer, as described above, the multiple phase demodulation data of the plurality of cycles of the chirp wave is mapped. Accordingly, the multiple phase demodulation data is sequentially read out from the RF buffer 43, and the Doppler spectrum and the fixed material spectrum obtained in each range are operated. Next, from the result obtained by calculating the spectrum for every cycle of the chirp wave, the power of the fixed material is generated in the A mode image of the range direction, and the parameters of the power, the average frequency, the dispersion or the like of the Doppler component are created as a color image of the A mode. This image data is averaged for a plurality of cycles of the chirp wave in accordance with the sweep speed, then transmitted to the monitor 63 through the DSC 61, and then displayed in the CWM mode.

Figure 12:
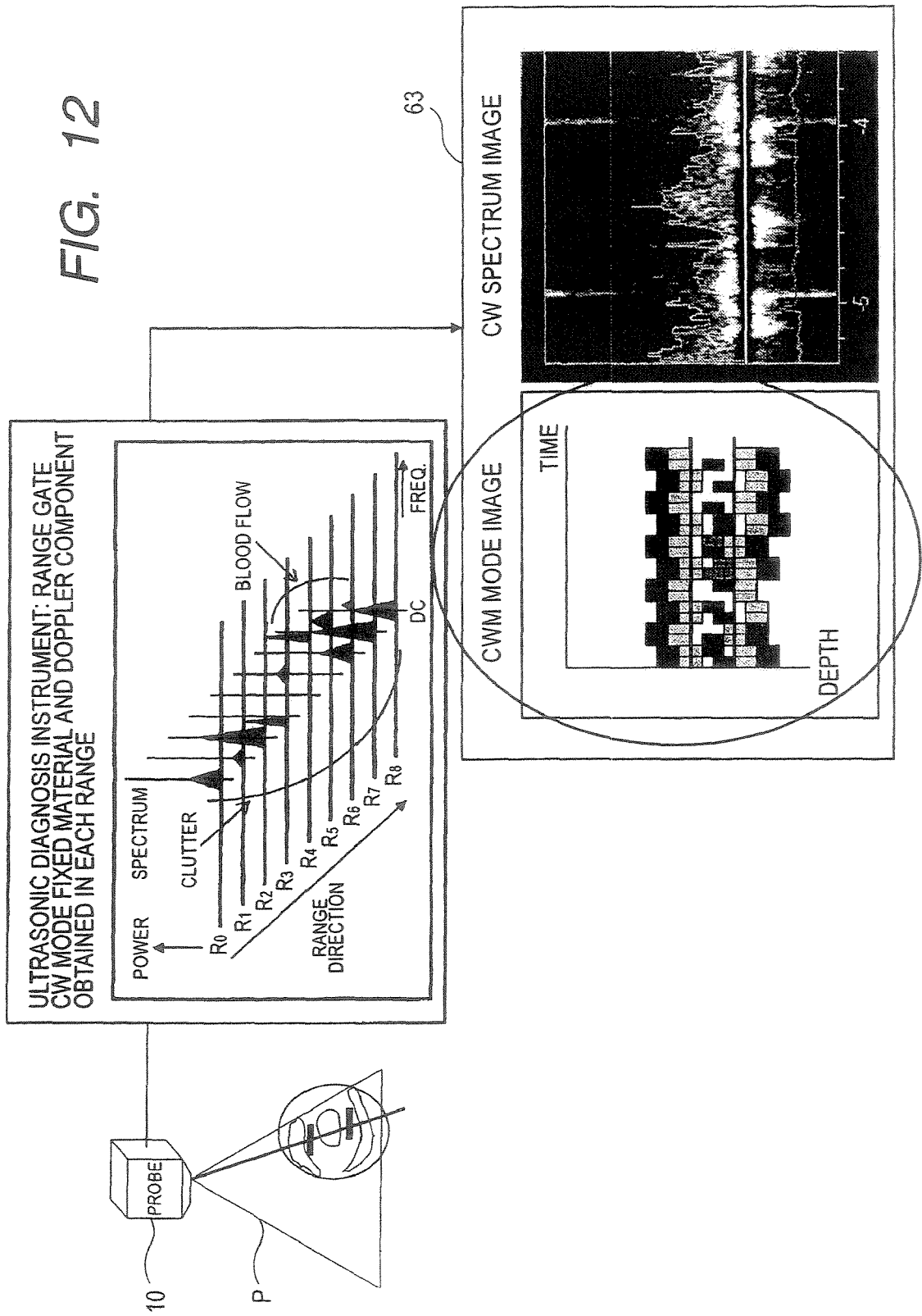
FIG. 12 is a diagram illustrating a process algorithm of a CWM mode.

In the CWM mode image shown in FIG. 12, the longitudinal axis corresponds to each range of the range direction, and the horizontal axis corresponds to the time base. The CWM mode image is displayed in real-time. The clutter is displayed in white and black, and the blood flow is displayed in color.

Process of CW Doppler Mode and Display

Figure 13:
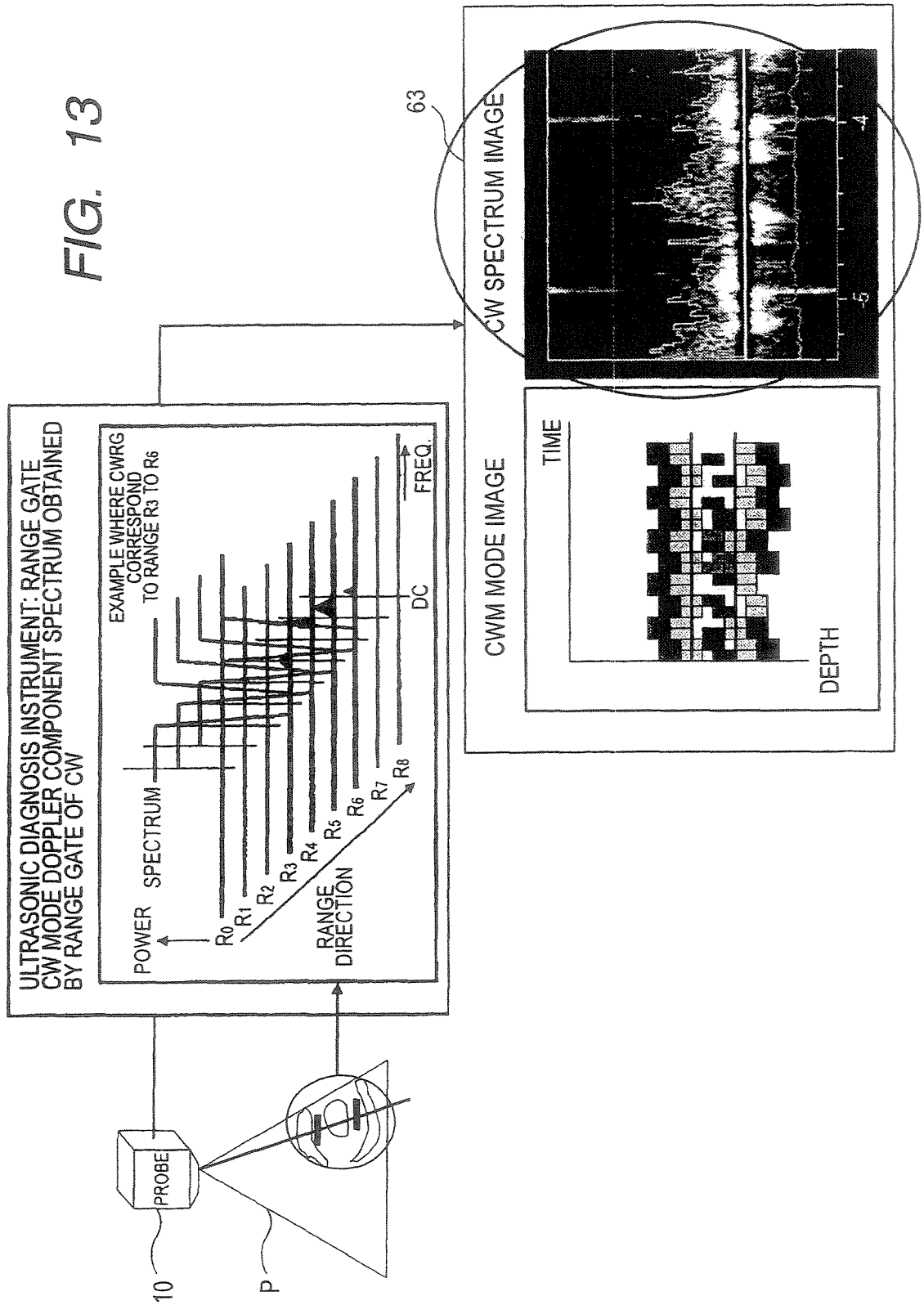
FIG. 13 is a diagram illustrating an algorithm of a range gate CW (RGCW) process in a CW Doppler mode.

Further, the process, which is performed by the CW range gate circuit 46, the CWRG process circuit 47, the LPF 48, the HPF 49, the frequency analyzer 50, and the CW Doppler mode display process circuit 51, will be described with reference to FIG. 13. In the RF buffer 43, as described above, the multiple phase demodulation data of the plurality of cycles of the chirp wave is mapped. Accordingly, the multiple phase demodulation data of a range, which belongs to the set range gate (CWRG), is sequentially read out from the RF buffer 43, and the Doppler spectrum and the fixed material spectrum obtained in each range are operated. In the example illustrated in FIG. 13, the ranges R3 to R6 correspond to the range gate CWRG. Next, from the result obtained by calculating the spectrum for every cycle of the chirp wave, the Doppler component whose band is separated by the HPF is obtained. The Doppler component is averaged for a plurality of cycles of the chirp wave in accordance with the sweep speed, and thus the data of the CW spectrum image is operated. This data is transmitted to the monitor 63 through the DSC 61, and the CW spectrum image is displayed on the monitor. As a result, as shown in FIG. 13, the CW spectrum image is displayed in which the longitudinal axis corresponds to the power spectrum of the Doppler component, and the horizontal axis corresponds to the frequency.

In addition, in addition to performing the simple addition in the range direction at the time of the spectrum addition in the range direction, the weight addition can also be performed.

The above-mentioned range gate circuit 46 generates the designation information of the range gate RG that has the designated location and width, and transmits the designated information to the CWRG process circuit 47 and the DSC 61.

The DSC 61 receives the designated information and displays the gamma indicating the designated location of the range gate RG on the B mode tomographic image.

For example, as shown in FIG. 2, the gammas correspond to two short straight lines which are parallel to each other. When viewing the gamma, the operator can discriminate the location on the tomographic image of the range gate RG, and switches the scan into the range gate CW mode. As a result, the CW spectrum that corresponds to the designated location is analyzed. The CWRG process circuit 47 receives the designated information, and analyzes the CW spectrum with respect to the range gate of the designated location and width, as described above.

For this reason, when the location and width of the range gate RG are varied, the operator operates the operator 16 so as to allow the signal of the varied information to be supplied to the controller 15. Thereby, the control signal, which is supplied from the controller, is transmitted to the CW range gate circuit 46, the designated information of the range gate of the new location and/or width is created, and the spectrum can be analyzed on the basis of the corresponding location and width.

Example of Simulation Using Phantom Model and Signal Process of Range Gate CW Mode In this case, a specific example of the simulation using the phantom model and the signal process is described by using the ultrasonic wave diagnosis instrument according to the above-mentioned embodiment.

As shown in FIG. 19, the experiment condition is set as follows, and the multiple phase modulation is performed on ranges RG of five locations set to phantoms. In this case, the width of the range is 0.5 mm.

$F$smaple=10 MHz,$F$tx=1 MHz,$F$sweep=1 KHz, $F$mod=500 Khz, and Anoise=−80 dB(to the clutter).  [Equation 3]

RG 46 mm,RG 48 mm,RG 50 mm,RG 52 mm, and RG 54 mm.  [Equation 4]

Figure 20:
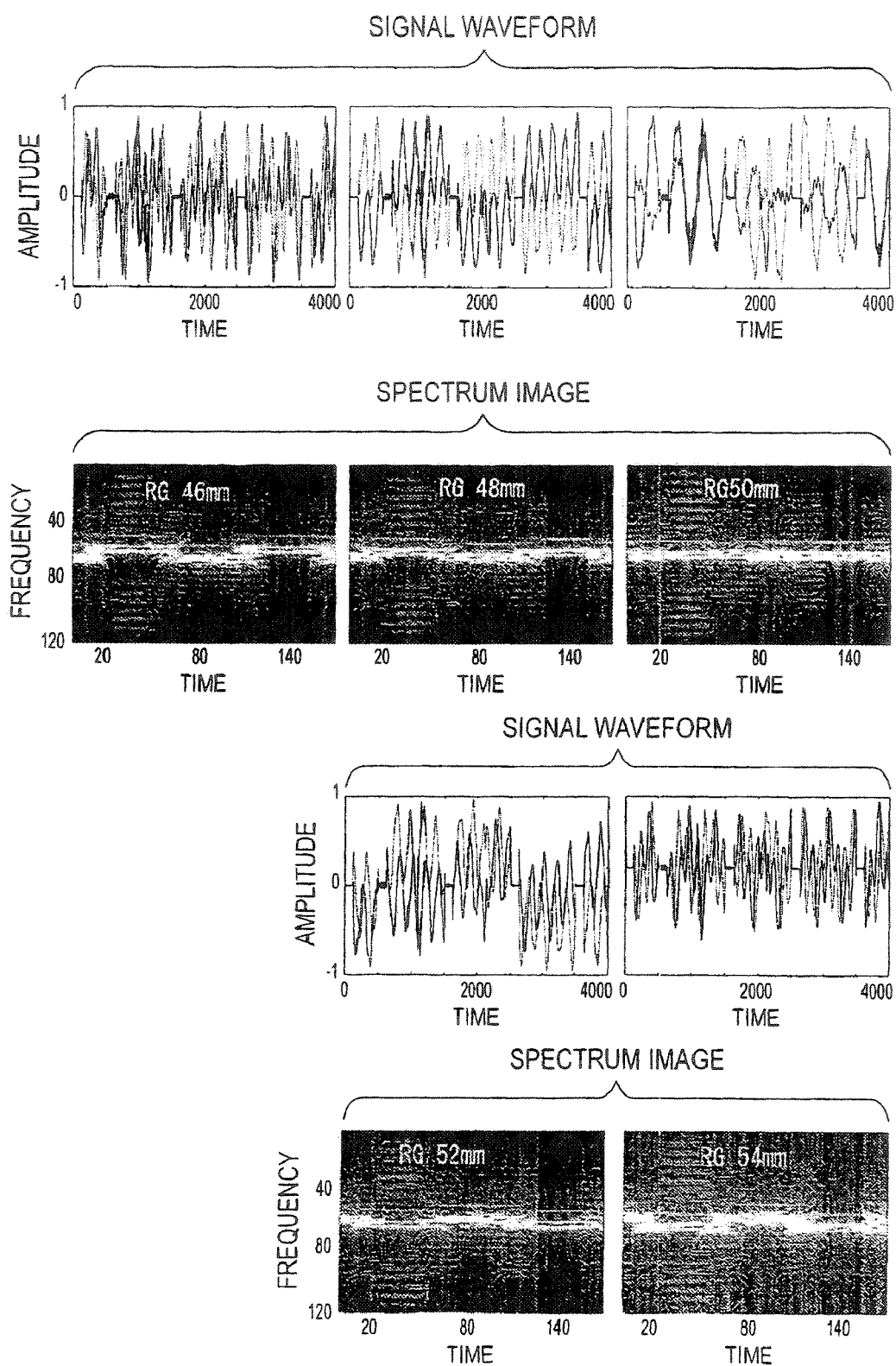
FIG. 20 is a graph illustrating a time variation of a spectrum and a time series signal for every range by the simulation.

The time variation of the spectrum and the time series signal (IQ data) for each range, which is obtained by the multiple phase modulation performed with respect to the phantom, are as shown in FIG. 20. These signal and time variation correspond to the result obtained by anyalyzing the demodulation data accumulated in the RF buffer 43.

FIG. 21 and FIG. 22, which is the temporal enlarged view of FIG. 21, show a signal presumption process of the cross region. According to this signal presumption, first, the time series data of the cross region is removed, and the data of the corresponding region is fixed to DC (0). Next, by using the effective data before and after the cross region in the time series direction, the system identification is performed with an AR model, and a parameter of a mathematical model is calculated. Next, the presumption signal of the cross region is a little much (to the extent that an overlapping region is obtained by using the actual data and the window function) generated from the noise by using the identified parameter. Next, the continuous wave is generated by window-weighting and adding the actual data and the presumption data to the overlapping region. In the process examples of FIGS. 21 and 22, weighting of '0 to π/2 of the COS function' is performed.

Next, the analysis of the spectrum of the rising gradient chirp wave and the spectrum of the falling gradient chirp wave is performed on the basis of the continuous wave generated by burying the cross region, and the power of the fixed material (clutter component) for each range, the power of the moving material (mainly, blood flow Doppler component), and the average speed, which are necessary for the CWM mode, are operated.

Next, the synthesis process of the spectrums of the rising component and the falling component is performed as shown in FIG. 23. Specifically, 1) the rising time series and the falling time series are cut such that the cross region is located at an end of the window function. 2) The Hanning window function is applied to the respective time series data so as to be subjected to the complex Fourier transform process. 3) The plus components and the minus components of the rising component spectrum and the falling component spectrum are operated. 4) The difference between the operated plus component and the minus component is operated, and an on-range component where the distance (depth) of each range is equal is extracted. In FIG. 24, the synthesis signal in each range is illustrated in (FIG. 24(A), the plus component/minus component of the spectrum is illustrated in (FIG. 24(B)), and the spectrum component of the on-range is illustrated in (FIG. 24(C)).

Figure 25A:
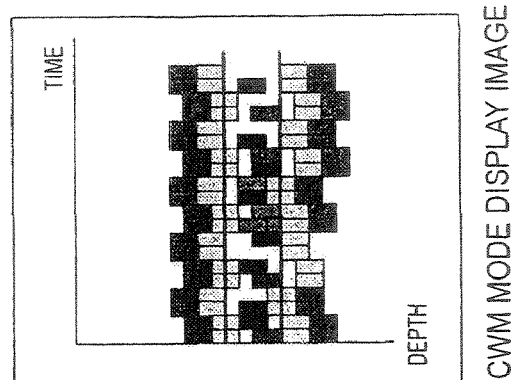
FIG. 25 is a diagram illustrating an operation process of a display parameter of a CWM mode image.
Figure 25B:
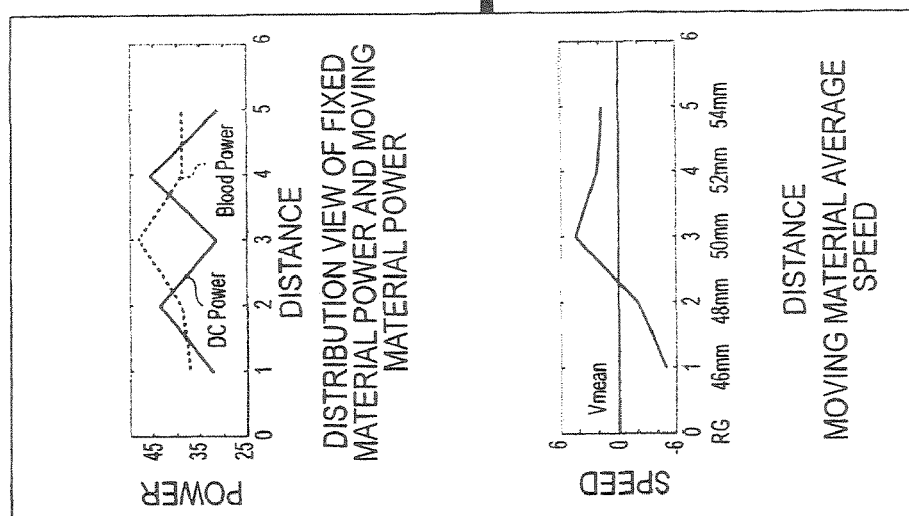
Figure 25C:
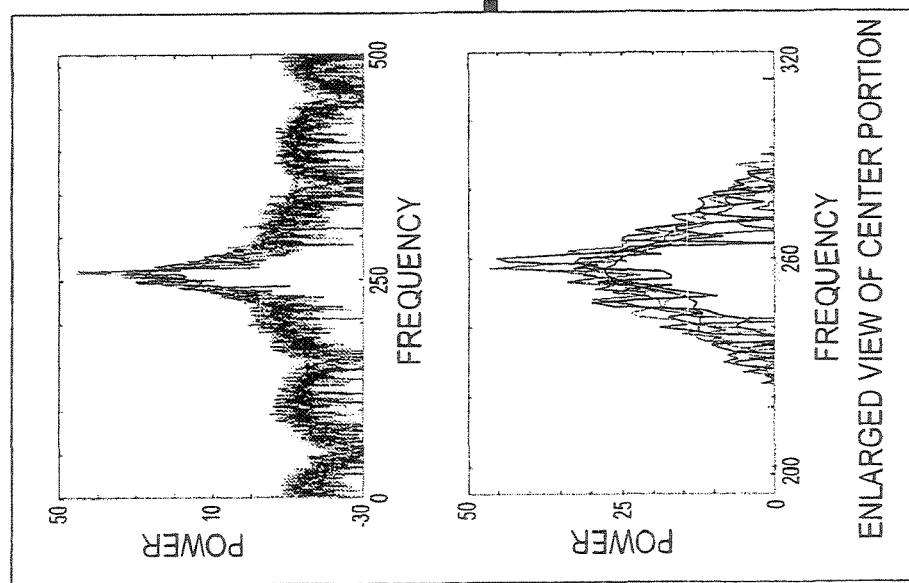

The operation process of the display parameter with respect to the CWM mode image is illustrated in FIG. 25. Specifically, as shown in FIG. 25(A), the multiple phase detection is performed in each range, and as shown in FIG. 25(B), the power component near the DC having passed through the LPF is operated by using the spectrum after removing the artifact. In addition, the component of the moving material after passing through the HPF is operated, and the average speed of the moving material after averaging the load from the moving material component after passing through the HPF is operated. Next, as shown in FIG. 25(C), for each range, the gradation of black and white is applied to the power of the fixed material, the power or average speed of the moving material is converted into the color data, and the CWM image where the longitudinal axis indicates a range direction and the horizontal axis indicates the time direction is displayed in real time.

In the meantime, the CW range gate process where the CW spectrum image is displayed as the CW Doppler mode image is performed as follows.

The analysis of the spectrum of the rising gradient chirp wave and the spectrum of the falling gradient chirp wave is performed from the continuous wave generated by burying the cross region, the artifact components of the fixed material and the moving material of the off-range where the distance is not equal are removed. Since the process until the removing process is the same as the CWM mode process, the process result thereof is used. Further, from the spectrum of an on-range, the fixed material component of the on-range is removed, and only the moving material component of the on-range is extracted. The moving material component of the on-range is subjected to the band restriction process, the spectrum interpolating expansion process, and the synthesis process of the continuous wave by the inversed Fourier transform process and the window weight addition in accordance with the observation time or the sampling frequency of the frequency analyzer of a next stage, and the weight addition process is performed in a range direction. The signal having subjected to these processes is output to the frequency analyzer.

Figure 26:
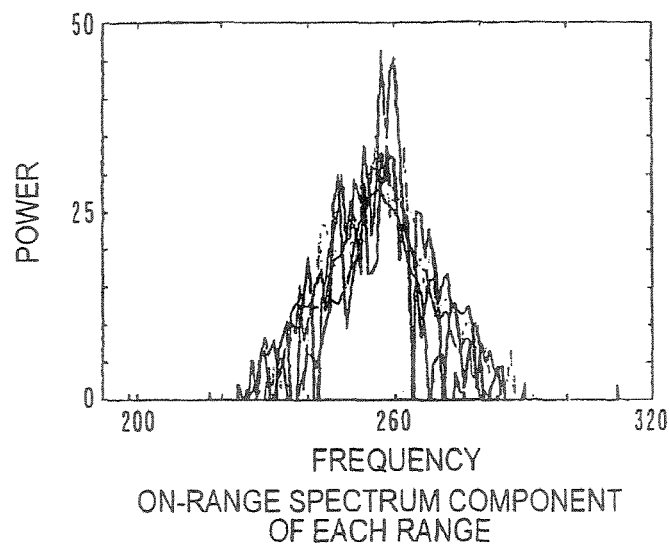
FIG. 26 is a diagram illustrating an on-range spectrum component of each range that is used for a continuous wave creating process for range gate CW.
Figure 27:
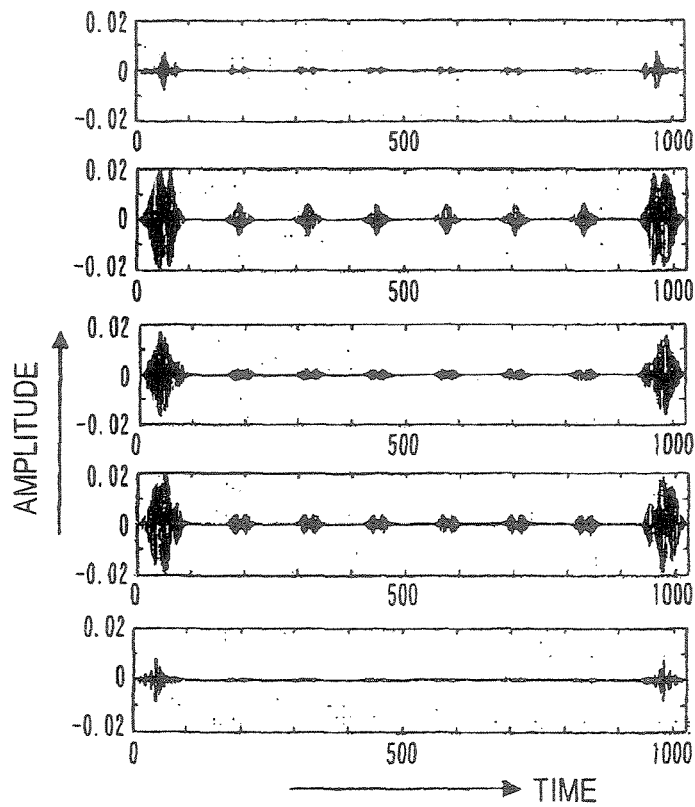
FIG. 27 is a diagram illustrating a continuous wave synthesized by subjecting a time component of a spectrum of FIG. 26 to an inversed FFT/scaling process.

The creation process of the continuous wave for range gate CW is described in detail with reference to FIGS. 26 and 27. The time component from the spectrum of the on-range where the artifact of FIG. 26 is removed is subjected to the inversed FFT process so as to generate the continuous wave. In this case, the clutter component is removed from the spectrum by the HPF process, but in the process example, the LPF is lowered, and the clutter component is made to pass through. Next, the Hanning window is applied to the complex signal having been subjected to the inversed FFT, the overlapping addition is performed with respect to the time series data that is necessary for the sampling of the frequency analyzer of the rear stage, and the waveform of FIG. 27 is created. In this process example, for the purpose of reducing the simulation load, the modulation frequency is raised. Therefore, the pitch conversion (the interpolation of the spectrum and scaling for cutting the DC center portion) is performed, and the frequency analysis load of the rear stage is reduced.

Figure 28A:
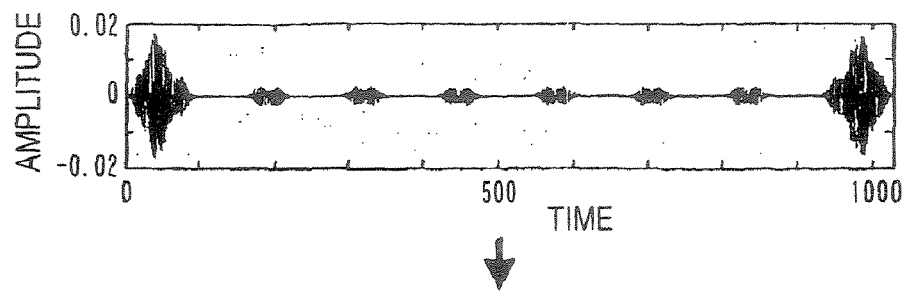
FIG. 28 is a diagram illustrating a synthesis of a continuous wave for range gate CW and CW range gating (CWRG).
Figure 28B:
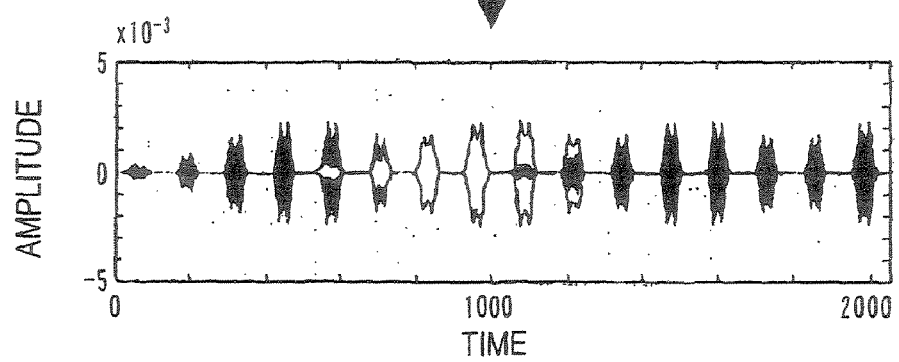
Figure 28C:
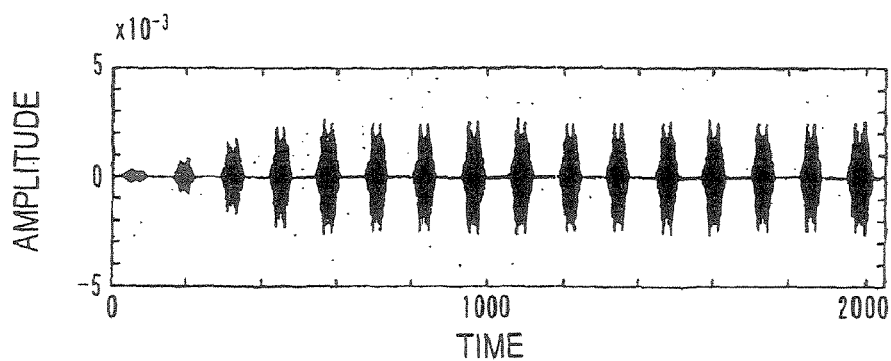

The synthesis of the continuous wave for range gate CW, and CW range gate process, and the display process thereof are illustrated in FIGS. 28 and 29. The continuous wave (FIG. 28(A)) that is generated in the pair of period intervals of the rising gradient chirp wave and the falling gradient chirp wave is cut by the Hanning window, and then added in an overlapping manner. As a result, the continuous wave (FIG. 28(B)) is generated. The continuous wave is generated for every range. At this time, the addition is made while considering that the plurality of range signals (time components and frequency components) which correspond to the width and the location of the range gate (contained in the range gate), and one continuous wave (FIG. 28(C)) is generated (this is referred to as continuous wave range gating (CWRG process)). In addition, in the weighting at the time of adding the plurality of ranges, weighting, such as a Gauss function, a rectangular function, a trapezoidal function, or the like, which corresponds to the width of the range gate, can be selected.

Figure 29A:
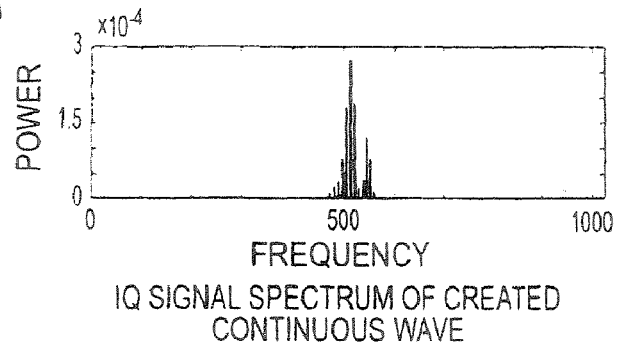
FIG. 29 is a diagram illustrating a sequence of a CW spectrum Doppler signal process and a display state of a RGCW spectrum image.
Figure 29B:
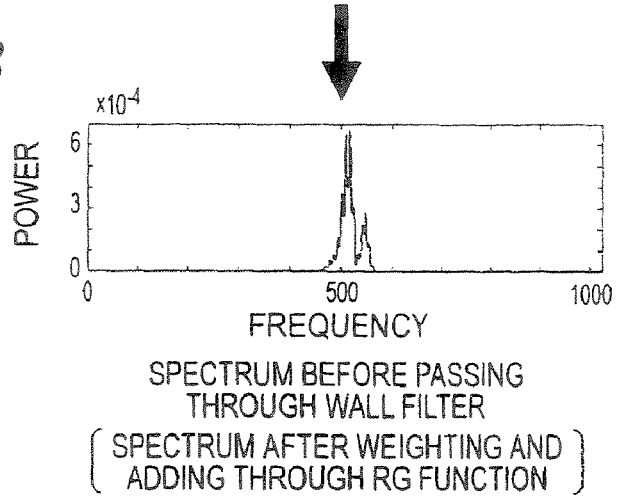
Figure 29C:
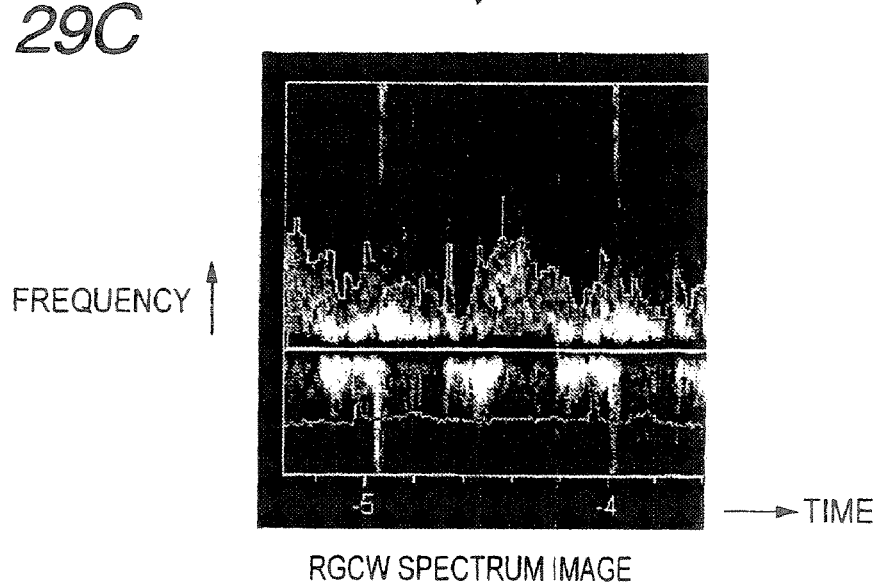

Next, the continuous signal, which is generated by the RGCW process, is spectrum-analyzed by the CW spectrum Doppler signal process (as an engineering terminology, referred to as periodgram) (FIGS. 29(A) and 29(B)), and the CW spectrum image (FIG. 29(C)) (a longitudinal axis indicates the frequency, and the horizontal axis indicates the time) is displayed. Further, FIG. 29(A) corresponds to the spectrum of the IQ signal of the continuous wave shown in FIG. 28(B), and FIG. 29(B) corresponds to the spectrum of the IQ signal of the continuous wave shown in FIG. 28(C).

Function and Effect

According to the above-mentioned embodiment, using the ultrasonic continuous wave, an ultrasonic wave Doppler diagnostic method, which is referred to as the range gate CW mode, is provided. That is, by performing the frequency modulation with respect to the transmitted ultrasonic continuous wave and interlocking (synchronizing) with the chirp waves of the rising gradient and the falling gradient at the time of the modulation at a predetermined timing, the multiple phase demodulation is performed with respect to the reception ultrasonic wave. The signal having been subjected to the multiple phase demodulation has the information of the distance direction on the same ultrasonic beam, and the signal components of the fixed material and the moving material, which correspond to each range (depth), and the signal components of the fixed material and the moving material, which do not correspond to each range, are contained while having different characteristics. The signal components of the fixed material and the moving material, which correspond to each range, are extracted by using these characteristics. The CWM mode where the information of the distance direction (that is, time direction) of the fixed material (clutter) and the moving material (blood flow) on the beam is displayed as the CWM mode image in white and black and a color, and the CW Doppler mode where the time variation of the spectrum of the data corresponding to the range gate (ROI: region of interest) on the beam is displayed as the CW spectrum image are provided. For this reason, the merit that the turnback of the continuous wave is not generated is available as it is, and the region of the blood flow signal is selected by avoiding the clutter region by the range gate so as to be observed. Therefore, it is possible to improve the Doppler analysis capability in which the depth of view is thick, and the blood flow speed is fast.

Therefore, when the valve regurgitation of the heart or the intermediate loss is observed, the invention is considered that it is clinically effective.

MODIFICATION

Hereinafter, the modifications which are applicable by the ultrasonic wave Doppler diagnosis instrument according to the present embodiment will be described.

First Modification

According to the first process, the sequential calculation is made by only using an on-range region, and the spectrum map is created. The first modification may be performed after the process according to the above-mentioned embodiment, and may be independently performed. That is, the difference '$R_B - R_A$' between the signal component (FIG. 6(B)) of the region $R_B$ shown in FIG. 5(A) and the signal component (FIG. 6(A)) of the region $R_A$, and the difference '$R_{E-RD}$' between the signal component (FIG. 6(D)) of the region $R_E$ and the signal component (FIG. 6(C)) of the region $R_D$ are sequentially calculated, and the spectrum map (FIG. 5(B)) is created.

An example where the spectrum obtained in the $R_A$ region of the rising gradient chirp wave and the $R_D$ region of the falling gradient chirp wave is used (that is, an example where a portion of the data during calculation of the CWM mode is used) will be described with reference to FIGS. 14 and 15.

For example, from the spectrum (FIG. 15(A)) that is obtained in the $R_A$ region of the chirp wave and the $R_D$ region of the chirp wave in the range R3, calculated are the center frequency Fc and the band width fbw of the spectrum (FIG. 15(B)) which are obtained by removing the component of the fixed material (near DC) by the above-mentioned difference. The HPF process and the complex BPF process are performed with respect to the time base (continuous) signal of each range on the basis of the information of the Doppler signal component corresponding to each range, and the Doppler component of each range is extracted. In the signal, the artifact where the frequency aligns is mixed, but by the addition of the range direction, the deterioration due to mixing is improved.

The range gate-added continuous wave signal contributes to the conventional Doppler analysis process and the spectrum display.

Second Modification

As shown in FIG. 16, according to a second modification, the reception is made with an ultrasonic continuous wave having been subjected to the frequency modulation, the transmission is not limited to the frequency modulation of the transmission continuous wave Tx, the continuous wave Tx is subjected to the amplitude modulation (AM), and the transmission is made by the interval that corresponds to the CW range gate. In addition, FIG. 17 illustrates a comparison example of a case in which the amplitude modulation is not performed.

By the AM modulation of the transmission wave Tx, the transmission energy of the continuous wave can be effectively used. In addition, there is an advantage in that the influence of the artifact other than the periphery of the range R1 is small.

However, since the spectrum of the reception wave Rx becomes intermittent, the signal process is necessary in which the continuous signal to which the gate is applied is locked to generate the continuous sine wave component (the DC component is cut).

Specifically, the continuous wave to which the gate is applied is input to one input terminal of the phase comparator, the output error signal is made to pass through the LPF (loop filter) so as to extract the low frequency component, the sine wave signal generating process is not performed which generates the frequency shift proportional to the DC value, and the output thereof is output to the other input terminal of the phase comparator. Here, the center frequencies of the sine wave signal generating process that generates the frequency shift are the center frequencies (DC) of the fixed material of the reception range direction, and correspond to the frequencies of the plus and the minus (the polarities are opposite to each other). For this reason, the continuous wave component corresponding to the moving material is continuously generated by a so-called PLL (Phase Locked Loop).

Thereby, the Doppler component of the high SN (Signal-to-Noise) ratio (it is presumptively generated from the burst) is obtained.

Third Modification

The third modification relates to the unit phase demodulation type. In the unit phase demodulation type, the phases of the transmission modulation and the reception modulation are not varied for each range.

Since the multiple phase demodulating type needs to perform the detection process of the plurality of ranges, the signal process load is weight. Therefore, by the unit phase demodulation type, the CWM mode display can be more easily provided to the device whose hardware size is reduced. As such, even if it is a single phase, the same process as the multiple phases can be performed.

Specifically, the varied BPF of the center frequency Fc is searched for every range, and the frequency is sequentially analyzed by the DFT (Discrete Fourier Transform). The frequency axes of the DFT are corrected for every range and joined in the chirp wave interval. Then the accumulated map of the clutter component and the Doppler component is created.

The difference of the spectrum of the entire frequency region is calculated from the accumulated map, and the information in each range is calculated. That is, the power of the fixed material component and the power of the moving material component are calculated and added up.

According to the single phase demodulation type, it is likely to be affected by the artifact, and it is suitable for the analysis of the range direction component. However, it is difficult to create the continuous wave component by any process. In addition, as described above, there are many cases that the advantage like small-sized hardware can be achieved. In order to decrease the above-mentioned inconvenience, the display of the power components of the clutter and the Doppler (corresponds to the M mode of the ultrasonic wave angio) may be used in the CWM mode as the application range.

Fourth Modification

The fourth modification will be described with reference to FIG. 18. This modification relates to another structure which detects the power of the fixed material/moving material of the on-range.

In the fourth modification, at the time of detecting the power of the fixed material/moving material of the on-range, among the plus components of the power spectrums of the rising gradient chirp wave and the falling gradient chirp wave, the component, which becomes twice as much as the power spectrum of the rising side (or the power spectrum of the falling side) is extracted and detected.

FIG. 18 shows the outline of the algorithm that extracts the on-range component from the plus component of the power spectrum of the chirp wave of the rising gradient/falling gradient. That is, first, the power spectrum plus component of the chirp wave of the rising/falling gradient Padd(f), the power spectrum component of the chirp wave of the rising gradient Pup(f), and the power spectrum component Pdn(f) of the chirp wave of the falling gradient are calculated.

Next, from the above-mentioned spectrums, the Padd(f), which simultaneously satisfied (Formula 1) and (Formula 2), is extracted as the component on the on-range.

[Equation 5]

$$Pup(f)*\alpha < Padd(f)/2 < Pup(f)*\beta \quad \text{(Formula 1)}$$

$$Pdn(f)*\alpha < Padd(f)/2 < Pdn(f)*\beta \quad \text{(Formula 2)}$$

(In this case, $\alpha$ and $\beta$ indicate variable parameters.)

In addition the functions $\alpha$ and $\beta$ can vary in a plurality of stages by an operator. For example, the functions $\alpha$ and $\beta$ vary according to the three stages of setting.

Setting 1: $\alpha=0.9$, and $\beta=1.1$

Setting 2: $\alpha=0.8$, and $\beta=1.2$

Setting 3: $\alpha=0.7$, and $\beta=1.3$ [Equation 6]

In the case of the setting 1, when compared with the setting 3, the detection sensitivity becomes lowered, but it is likely to be affected by the artifact.

Fifth Modification

The fifth modification will be described with reference to FIG. 30. The fifth modification relates to a structure which uses a process method for suppressing the lowering of the frequency resolution according to the condition of the chirp wave. According to the present modification, it is possible to further improve the distance resolution.

FIG. 30(A) shows the chirp wave used for the frequency modulation at the time of transmission, in which the horizontal axis indicates the time, and the longitudinal axis indicates the frequency. FIG. 30(B) shows the chirp wave used for the multiple phase FM demodulation at the time of reception, and forms a pair together with the chirp wave shown in FIG. 30(A). In FIG. 30(B), the horizontal axis indicates the time, and the longitudinal axis indicates the frequency. FIG. 30(C) shows a demodulation signal demodulated through the multiple phase demodulation by the chirp wave shown in FIG. 30(B), in which the horizontal axis indicates the time, and the longitudinal axis indicates the frequency.

As shown in FIG. 30(A), if one cycle of the chirp wave is set to $\Delta t$ and the variation of the frequency is set to $\Delta f$, depending on the conditions of the $\Delta t$ and $\Delta f$ of the chirp wave, the inclination, which cannot be disregarded, may be generated in the clutter component and the Doppler component of the on-range shown in FIG. 30(C). FIG. 30(D) shows an example of the clutter signal of the on-range having the inclination. As shown in FIG. 30(D), the inclination existing in the signal of the on-range means that the width ΔB exists in the frequency direction of the on-range signal.

It is confirmed that the inclination, which appears in the on-range signal, increases, when the inclination of the chirp wave increases, that is, when Δt is small but Δf is large. In addition, as shown in FIG. 30(D), the direction of the inclination, which appears in the on-range signal, is alternately varied, and the same inclination as the direction of the inclination of the chirp wave is shown. Therefore, it is assumed that the inclination appears in the on-range signal due to the gradient of the chirp wave. With respect to the specific and accurate reason, the detailed analysis is necessary, but it is assumed as one reason that there is a limit in the resolution of the frequency analyzer.

In the meantime, as described above, the spectrum of the demodulation signal is subjected to the addition process and the subtraction process so as to be divided into the on-range signal and the off-range signal. For this reason, the inclination in which the direction is alternately varied is exists in the on-range signal, and the width appears in the frequency direction. In this case, the resolution of the frequency is deteriorated.

Accordingly, the time direction in the frequency analysis (FFT) is varies in accordance with the inclined direction of any one of the on-range signal and the chirp wave, so that it is possible to avoid the resolution of the frequency from being deteriorated due to the inclination of the chirp wave, as described above. That is, actually, since the inclined direction of the on-range signal is not alternately varied but the inclination is constant, it is possible to reduce the influence of the inclination of the on-range signal with respect to the spectrum. The arrow shown in FIG. 30(D) indicates the time direction in the frequency analysis. Both sides of the time direction may be opposite to each other.

Even though the inclination exists in the on-range signal, if a predetermined frequency resolution can be maintained, the inclination (2Δf/Δt) of the chirp wave can be set so as to be further larger. If the inclination of the chirp wave can be set to be further larger, Δt of the chirp wave shown in FIG. 30(A) and the phase shift amount Δt' of the chirp wave for the multiple phase FM demodulation according to the depthwise direction shown in FIG. 30(B) are set to be further smaller. As a result, it is possible to improve the distance resolution. That is, the time direction in the frequency analysis is varied and the influence of the inclination appearing in the on-range signal is avoided. It is possible to use the condition in which the distance resolution is improved while maintaining the frequency resolution.

The above-mentioned embodiment and the modification have been described above, but the ultrasonic wave Doppler diagnosis instrument is not limited to the above-mentioned structures. In addition, the known technologies can be properly combined and embodied within a range of the spirit of the invention described in the appended claims, and the invention includes various changes and modifications.

The invention claimed is:

1. An ultrasonic wave Doppler diagnosis instrument, comprising:
a frequency modulation unit configured to frequency-modulate, based on an alternating combination of an up-chirp wave and a down-chirp wave, a sine wave so as to generate an ultrasonic continuous wave;
a transmission unit configured to transmit the ultrasonic continuous wave;
a reception unit configured to receive a reflective wave of the ultrasonic continuous wave;
a demodulation unit configured to multiple-phase-FM (frequency modulation)-demodulate the reflective wave for a range in a range direction by varying phases of reception modulation for each range while interlocking in synchronization with the frequency modulation frequency modulated by the frequency modulation unit, and to generate a reception signal in the range in a separated state;
an extraction unit configured to remove an outside signal outside the range and to extract a signal of a Doppler component within the range;
and a presentation unit configured to present information using a signal of the Doppler component based on the extracted signal,
wherein the demodulation unit includes an extrapolation unit configured to remove a cross region where gradients of the two chirp waves are opposite to each other in a polarity and to extrapolate a signal on one of a frequency axis and a time axis.

2. The ultrasonic wave Doppler diagnosis instrument according to claim 1,
wherein the demodulation unit classifies a plurality of regions as within the range or outside the range, detects each region of the plurality of regions, and creates the reception signal, while using a complementary pair detection signal of the frequency modulation used for the frequency modulation and demodulation.

3. The ultrasonic wave Doppler diagnosis instrument according to claim 1, wherein the presentation unit includes a frequency analysis unit configured to vary a time direction in accordance with a direction of a gradient of the reception signal so as to perform frequency analysis.

4. The ultrasonic wave Doppler diagnosis instrument according to claim 1, wherein
the extraction unit is configured to extract a fixed material component signal and the Doppler component signal in the range; and
the presentation unit includes a first display controller configured to apply white and black gradations to the fixed material component signal obtained for the range, to apply a color to the Doppler component signal, and to cause a distribution diagram in which a longitudinal axis indicates the range and a horizontal axis indicates time to be displayed on a display.

5. The ultrasonic wave Doppler diagnosis instrument according to claim 1, wherein
the extraction unit is configured to extract a fixed material component signal and the Doppler component signal in the range; and
the presentation unit includes:
a first display controller configured to apply white and black gradations to the fixed material component signal obtained for the range, to apply a color to the Doppler component signal, and to cause a distribution diagram in which a longitudinal axis indicates the range and a horizontal axis indicates time to be displayed on a display;
a range gate setting unit configured to set a range gate as a target region which can freely adjust a location and a width in the range direction;
a second extraction unit configured to extract a Doppler component in a second range corresponding to the range gate; and
a second display controller configured to cause a power spectrum of the Doppler component in the second range corresponding to the range gate as a distribution diagram in which a longitudinal axis indicates a frequency and a horizontal axis indicates time to be displayed on the display.

6. The ultrasonic wave Doppler diagnosis instrument according to claim 1, further comprising:
a range gate setting unit configured to set a range gate as a target region which can freely adjust a location and a width in the range direction.

7. The ultrasonic wave Doppler diagnosis instrument according to claim 2,
wherein the demodulation unit uses two chirp waves as the complementary pair detection signal, the two chirp waves having modulation frequencies having a rising gradient and a falling gradient that are swept to each other, and
the demodulation unit includes a region control unit configured to control a time width of a region where gradients of the two chirp waves are opposite to each other in polarity.

8. The ultrasonic wave Doppler diagnosis instrument according to claim 2,
wherein the demodulation unit uses two chirp waves as the complementary pair detection signal, the two chirp waves having modulation frequencies having a rising gradient and a falling gradient that are swept to each other, and
the demodulation unit includes a control unit configured to control a modulation frequency corresponding to a reciprocal number of a modulation period of the two chirp waves and a sweep frequency of the two chirp waves in accordance with mode selection between a mode in which a time resolution has a priority with respect to scanning on each beam by transmission of the ultrasonic continuous wave and a mode in which a frequency resolution has a priority with respect to scanning on each beam by transmission of the ultrasonic continuous wave.

9. The ultrasonic wave Doppler diagnosis instrument according to claim 2,
wherein the demodulation unit uses two chirp waves as the complementary pair detection signal, the two chirp waves having modulation frequencies having a rising gradient and a falling gradient that are swept to each other.

10. The ultrasonic wave Doppler diagnosis instrument according to claim 6,
wherein the extraction unit is configured to extract a Doppler component in a second range which corresponds to the range gate set by the range gate setting unit; and
the ultrasonic wave Doppler diagnosis instrument further comprises a first display controller configured to perform weight addition on the Doppler component in the second range, and to cause a power spectrum of the Doppler component in the second range as a distribution diagram in which a longitudinal axis indicates a frequency and a horizontal axis indicates time to be displayed on a display.

11. The ultrasonic wave Doppler diagnosis instrument according to claim 4,
wherein the demodulation unit creates the reception signal by using chirp waves as a complementary pair detection signal, the chirp waves having modulation frequencies having a rising gradient and a falling gradient that are swept to each other, and
the first display controller operates a spectrum of the fixed material component and a spectrum of the Doppler component that are obtained in the range of the range direction along a beam on the basis of multiple phase demodulation data of a plurality of cycles of the chirp wave, creates power of the fixed material from the spectrum operated for each cycle of the chirp wave on an A mode image of the range direction, creates at least one parameter among power of the Doppler component, an average frequency, and dispersion on an A mode color image, and averages the A mode image and the A mode color image for each cycle of the chirp wave in accordance with a sweep speed of the chirp wave so as to be displayed as a continuous wave M mode.

12. The ultrasonic wave Doppler diagnosis instrument according to claim 7,
wherein the region control unit is configured to control at least one of a modulation frequency corresponding to a reciprocal number of a modulation period of the two chirp waves and a location of the range direction.

13. The ultrasonic wave Doppler diagnosis instrument according to claim 10,
wherein the demodulation unit creates the reception signal by using chirp waves as a complementary pair detection signal, the chirp waves having modulation frequencies having a rising gradient and a falling gradient that are swept to each other, and
the second display controller operates a spectrum of the fixed material component and a spectrum of the Doppler component that are obtained in the range of the range direction on the basis of multiple phase demodulation data of a plurality of cycles of the chirp wave, operates a signal of the Doppler component according to the range gate whose band is separated by any one of a high pass filter and a band pass filter from the spectrum operated for each cycle of the chirp wave, and averages the obtained signal of the Doppler component for each cycle of the chirp wave in accordance with a sweep speed of the chirp wave so as to be displayed as a continuous wave spectrum image.

14. The ultrasonic wave Doppler diagnosis instrument according to claim 12,
wherein the region control unit is configured to automatically control the modulation frequency in accordance with a location of the range direction.

15. An ultrasonic wave Doppler diagnosis instrument, comprising:
a transmitter that frequency-modulates, based on an alternating combination of an up-chirp wave and a down-chirp wave, a sine wave so as to generate an ultrasonic continuous wave, and transmits the ultrasonic continuous wave;
a receiver that receives and multiple-phase-FM-demodulates a reflective wave of the transmitted ultrasonic continuous wave for a range in a range direction by varying phases of reception modulation for each range while interlocking in synchronization with the frequency modulation performed by the transmitter to generate a reception signal in the range;
an extraction unit configured to remove an outside signal outside the range and to extract a signal of a Doppler component within the range; and a presentation unit configured to present information using a signal of the Doppler component based on the generated extracted signal, wherein the receiver includes an extrapolation unit configured to remove a cross region where gradients of the two chirp waves are opposite to each other in a polarity and to extrapolate a signal on one of a frequency axis and a time axis.

* * * * *